(12) United States Patent
Choi et al.

(10) Patent No.: US 9,491,948 B2
(45) Date of Patent: Nov. 15, 2016

(54) **COMPOSITION COMPRISING *STREPTOMYCES SCOPULIRIDIS* KR-001 STRAIN, OR CULTURE BROTH THEREOF AS ACTIVE INGREDIENT FOR WEED CONTROL**

(71) Applicants: KOREA RESEARCH INSTITUTE OF CHEMICAL TECHNOLOGY, Daejeon (KR); KOREA RESEARCH INSTITUTE OF BIOSCIENCE AND BIOTECHNOLOGY, Daejeon (KR)

(72) Inventors: Jung Sup Choi, Daejeon (KR); Young-Sook Kim, Gyeonggi-do (KR); Boyoung Lee, Daejeon (KR); Jae Deok Kim, Chungcheongnam-do (KR); Young Kwan Ko, Daejeon (KR); Gyu Hwan Yon, Daejeon (KR); Chang Jin Kim, Daejeon (KR); Dong Jin Park, Daejeon (KR); Yoon Jung Ju, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 14/621,765

(22) Filed: Feb. 13, 2015

(65) Prior Publication Data

US 2015/0230477 A1 Aug. 20, 2015

Related U.S. Application Data

(63) Continuation-in-part of application No. PCT/KR2013/007279, filed on Aug. 13, 2013.

(30) Foreign Application Priority Data

Aug. 14, 2012 (KR) ........................ 10-2012-0088828
Jul. 31, 2013 (KR) ........................ 10-2013-0091223

(51) Int. Cl.
*A01N 63/00* (2006.01)
*A01N 63/02* (2006.01)
*C12N 1/20* (2006.01)

(52) U.S. Cl.
CPC ............... *A01N 63/00* (2013.01); *A01N 63/02* (2013.01); *C12N 1/20* (2013.01)

(58) Field of Classification Search
None
See application file for complete search history.

(56) References Cited

U.S. PATENT DOCUMENTS 6,524,577 B1 2/2003 Lehman et al.
2012/0028799 A1 2/2012 Martin et al.

FOREIGN PATENT DOCUMENTS

KR 100461579 B1 12/2004
KR 100477890 B1 3/2005

OTHER PUBLICATIONS

Macedo, J A et al., "Optimization of medium composition for transglutaminase production by a brazilian soil Streptomyces ep.," Electronic Journal of Biotechnology, Oct. 15, 2007, vol. 10, No. 4, pp. 618-626.
PCT International Search Report for Intl. App. No. PCT/KR2013/007279, from which the instant application is based, 4 pgs.
Basak et al., "Utilization of Carbon and Nitrogen Sources by Streptomyces kanamyceticus for Kanamycin Production," Antimicromal Agents and Chemotherapy, vol. 4, No. 1, Jul. 1973, pp. 6-10.
Berdy, "Thoughts and Facts About Antibiotics: Where We Are Now and Where We Are Heading," The Journal of Antibiotics, vol. 65, 2012, pp. 385-395.
Burg et al., "Avermectins, New Family of Potent Anthelmintic Agents: Producing Organism and Fermentation," Antimicrobial Agents and Chemotherapy, vol. 15, No. 3, Mar. 1979, pp. 361-367.
Hwang et al., "Isolation of Sangivamycin from *Streptomyces* sp. A6497 and its Herbicidal Activity," Journal of Microbiology and Biotechnology, vol. 15, No. 2, 2005, pp. 434-437.
Kahan et al., "Thienamycin, a new beta-lactam antibiotic. I. Discovery, taxonomy, isolation and physical properties," The Journal of Antibiotics, vol. 32, No. 1, Jan. 1979, pp. 1-12.
Miao et al., "Daptomycin Biosynthesis in Streptomyces roseosporus: Cloning and Analysis of the Gene Cluster and Revision of Peptide Stereochemistry," Microbiology, vol. 151, 2005, pp. 1507-1523.
Michalik et al., "Monophenol Monooxygenase and Lincomysin Biosynthesis in Streptomyces lincolnensis," Antimicrobial Agents and Chemotherapy, vol. 8, No. 5, Nov. 1975, pp. 526-531.

*Primary Examiner* — Alton Pryor
(74) *Attorney, Agent, or Firm* — Fredrikson & Byron, P.A.

(57) ABSTRACT

Disclosed herein is a composition containing a novel strain *Streptomyces scopuliridis* KR-001 strain or a culture broth thereof as an active ingredient for weed control. More particularly, the *Streptomyces scopuliridis* KR-001 strain of the present invention, culture broth thereof, or culture fraction shows an excellent weed-killing ability on grass weeds, broadleaf weeds, and hard-to-control weeds, and a medium composition containing a carbon source and a nitrogen source in an optimal condition may significantly increase yield of an active material produced by the strain with low cost. Therefore, the strain can be usefully employed to a herbicide composition for weed control and a method for weed control.

7 Claims, 17 Drawing Sheets

Control    1    1/2    1/4

FIG 14

| | Chemical | 1000 | 500 | 250µg mL⁻¹ |
|---|---|---|---|---|
| CK | EA fr. | | | |
| | Bialaphos | | | |
| | Glufosinate | | | |

Untreated

Bennet broth

Potato starch

Corn starch

Maltose

Soluble starch

Untreated | Bennet broth

Yeast extract | Beef extract | Soybean powder

Untreated | Bennet broth | Potato starch + Soybean powder

Untreated   Bennet broth   Optimum media

SEQUENCE LISTING

<160> NUMBER OF SEQ ID NOS: 1

<210> SEQ ID NO 1
<211> LENGTH: 1359
<212> TYPE: DNA
<213> ORGANISM: Streptomyces sclerotialus

<400> SEQUENCE: 1

```
gacgaacgct ggcggcgtgc ttaacacatg caagtcgaac gatgaagcct ttcggggtgg      60
attagtggcg aacgggtgag taacacgtgg gcaatctgcc cttcactctg ggacaagccc     120
tggaaacggg gtctaatacc ggataatact tctgcctgca tgggcgggg ttgaaagctc     180 cggcggtgaa ggatgagccc gcggcctatc agcttgttgg tggggtgatg gcctaccaag     240
gcgacgacgg gtagccggcc tgagagggcg accggccaca ctgggactga gacacggccc     300
agactcctac gggaggcagc agtggggaat attgcacaat gggcgaaagc ctgatgcagc     360
gacgccgcgt gagggatgac ggccttcggg ttgtaaacct ctttcagcag ggaagaagcg     420
aaagtgacgg tacctgcaga agaagcgccg gctaactacg tgccagcagc cgcggtaata     480
cgtagggcgc aagcgttgtc cggaattatt gggcgtaaag agctcgtagg cggcttgtcg     540
cgtcggatgt gaaagcccgg ggcttaaccc cgggtctgca ttcgatacgg gcaggctaga     600
gtgtggtagg ggagatcgga attcctggtg tagcggtgaa atgcgcagat atcaggagga     660
acaccggtgg cgaaggcgga tctctgggcc attactgacg ctgaggagcg aaagcgtggg     720
gagcgaacag gattagatac cctggtagtc cacgccgtaa acgttgggaa ctaggtgttg     780
gcgacattcc acgtcgtcgg tgccgcagct aacgcattaa gttcccgcc tggggagtac     840 ggccgcaagg ctaaaactca aaggaattga cggggggcccg cacaagcagc ggagcatgtg     900
gcttaattcg acgcaacgcg aagaaccta ccaaggcttg acatacaccg gaaacggcca     960
gagatggtcg cccccttgtg gtcggtgtac aggtggtgca tggctgtcgt cagctcgtgt    1020
cgtgagatgt tgggttaagt cccgcaacga gcgcaaccct tgttctgtgt tgccagcatg    1080
cctttcgggg tgatggggac tcacaggaga ctgccggggt caactcggag gaaggtgggg    1140
acgacgtcaa gtcatcatgc cccttatgtc ttgggctgca cacgtgctac aatggccggt    1200
acaatgagct gcgatgccgt gaggcggagc gaatctcaaa aagccggtct cagttcggat    1260
tggggtctgc aactcgaccc catgaagtcg gagttgctag taatcgcaga tcagcattgc    1320
tgcggtgaat acgttcccgg gccttgtaca caccgcccg                           1359
```

US 9,491,948 B2

COMPOSITION COMPRISING *STREPTOMYCES SCOPULIRIDIS* KR-001 STRAIN, OR CULTURE BROTH THEREOF AS ACTIVE INGREDIENT FOR WEED CONTROL

CROSS-REFERENCES TO RELATED APPLICATION

This patent application is a continuation-in-part of and claims the benefit of priority from International PCT Application No. PCT/KR2013/007279 filed Aug. 13, 2013, Korean Patent Application No. 10-2013-0091223, filed on Jul. 31, 2013, and Korean Patent Application No. 10-2012-0088828, filed on Aug. 14, 2012, the contents of which are incorporated herein by reference.

BACKGROUND OF THE INVENTION

1. Field of the Invention

The present disclosure relates to a novel *Streptomyces scopuliridis* strain having a weed-killing activity and a medium composition for mass production of the strain.

2. Description of the Related Art

Since there are numerous types of weeds, various classification methods exist. General classification methods used in agriculture include classification methods depending on life cycle and shapes of weeds. According to the classification method depending on a shape, weeds are classified into grass weeds, broadleaf weeds, cyperaceae weeds, and so forth depending on the shapes of weeds. According to classification method depending on the life cycle, weeds are classified into annual weeds, biennial weeds, perennial weeds, and so forth depending on how long the weeds live.

Grass weeds have well-distinguishable internodes in a stem, and alternate leaves stretching from nodes, wherein the leaves are divided into leaf sheaths to surround the stem for protection and a leaf blade in which leaf veins in narrow long shapes are formed in parallel. Grass weeds include *Echinochloa utilis, Digotaris sanguinalis, Alopecurus aequalis, Setaria viridis, Phragmites communis, Miscanthus sinensis*, and so forth. A broad leaf weed is a plant which does not belong to grass weeds or sedge weeds and literally refers to weeds having relatively broad leaves. A leaf, which is mostly in an oval shape, an eggshape, or a needle shape, has veins interlaced like a net. Numerous weeds frequently appearing around us are included in this category such as *Conyza Canadensis, Trifolium repens, Artemisia princes, Cardamine komarovi, Amaranthus mangostanus, Monochoria vaginalis* var. *plantaginea, Potamogeton franchetii*, and *Bidens tripartite*. Although weeds belonging to sedges share similar features with grass weeds, sedge weeds are distinguished by the fact that cross section of a stem is mostly in a triangle shape and there is no ligule or auricle. A leaf is narrow and has a ridge, and a pointed end. Also, a small flower is hung at a spikelet. Examples include *Cyperus microiria, Cyperus serotinas, Eleocharis kuroguwai ohwi, Scirpus fluviatilis, Scirpus juncoides Roxb*, and so forth.

*Sciyos angulatus* L., which is a naturalized annual plant of family Cucurbitaceae originated from North America, is a weed collectively appears, in domestically, residential areas, as well as, riverside, roadside, railroads, and farmland to thereby seriously destroy the ecosystem. Thus, *Sciyos angulatus* L. is designated as Invasive Alien Plant under Protection of Wild Fauna and Flora Act by Ministry of Environment. Since *Sciyos angulatus* L. vigorously grows, produces a large amount of seeds, and forms a colony to grow, *Sciyos angulatus* L. causes herbaceous plants and trees to be withered by covering the plants and trees and inhibiting photosynthesis; changes in biodiversity by depriving and disturbing water and nitrogen in soil to thereby destroy existing vegetation; and also causes direct damage to human and livestock by inducing dermatitis due to a prickle on a surface of the seed. Currently, *Sciyos angulatus* L. is distributed to whole areas of Korea, and the distribution area thereof has been spearing, thereby leading to serious damage. Thus it is urgently required to develop a control technique for *Sciyos angulatus* L. control.

A method for removing *Sciyos angulatus* L. known so far is to cut or pull out plantlet which needs intensive labor. *Sciyos angulatus* L. which appears in some farms, may be partially controlled by using a non-selective organic synthetic herbicide such as glyphosate, however, control using an organic synthetic herbicide is extremely limited in practical because major birthplace and habitat of *Sciyos angulatus* L. are riverside, roadside, or residential areas where people live.

Moreover, problems caused by continuous use of an organic synthetic herbicide have been raised such as appearances of resistant weeds, potential influence on the ecosystem, and environmental pollution. In addition, as interest in environmentally friendly agriculture is increased due to an increase in income and the trend of emphasizing quality of life, in various countries of the world, regulation for reducing a use of a synthetic agricultural pesticide is strengthened. Therefore, it becomes more difficult to control *Sciyos angulatus* L. mainly appearing residential areas by using the conventional organic synthetic herbicide.

Thus, it is urgently required a technique for environmental friendly control of *Sciyos angulates* L. by using a natural substance or a biochemical preparation which can be easily degraded under the natural condition and has low toxicity to human and livestock.

Although an organic synthetic herbicide has been used for a long time due to the low cost and the high weed-killing activity, an interest has been increased to develop an environmentally friendly herbicide which is biodegradable and has low toxicity and selectivity because of appearance of resistant weeds and environmental pollution caused by continuous use. In particular, a material having a weed-killing activity produced by a microorganism including *actinomyces* has high efficiency and an environmentally friendly property, and thus the material has been noted as an experimental material and also for industrial application.

*Actinomyces* including *Streptomyces* sp., which is a gram-positive soil microorganism growing in a spawn form, produces various types of beneficial secondary metabolites in addition to an antibiotic material such as a herbicide. Thus, *actinomyces* has been received attention by researchers in term of study or an industrial application. Examples of a material having a weed killing activity, to which a secondary metabolite produced by *actinomyces* is applied, include herbicidin and herbimycin produced by *Streptomyces saganonensis*, anismycin produced by *S. actinomycetes*, bialaphos produced by *S. viridochromogenes*, albucidin produced by *S. albus* subsp. chlorinus NRRL B-24108, and glufosinate-ammonium isolated from *S. viridichromogenes* and *S. hygroscopicus*. Among them, bialphos and ansamitocins are commercialized and sold.

Despite of many cases of study, it is extremely limited to develop a natural and safe herbicide for weed control having an excellent weed-killing activity and low toxicity. Also, most of microorganism herbicides or herbicides derived from a plant under study and development are targeted to weeds appearing in farmland. Thus, it is still required to discover a novel microorganism which can be used as an environmentally friendly natural pesticide having the excellent weed-killing activity and low toxicity. Also, there is an emerging need to select an optimized medium which can expand growth of a microorganism and improve production of an active material while economically reducing a cost to increase a value of the *Streptomyces* sp. strain in an application as a material for natural herbicide.

For culture of a microorganism, saccharides including glucose, sugar, and maltose, etc., a glucose extract, and various types of starch are used as a carbon source; and an organic nitrogen source such as a beef extract, a malt extract, an yeast extract, soybean meal, and peptone and an inorganic nitrogen source such as ammonia water, ammonia sulfate $((NH_4)_2SO_4)$, urea, and nitrate salts are used as a nitrogen source. In addition, a trace element such as a mineral and a vitamin is used to help bacterial growth and production of a secondary metabolite. These are most essential elements for culture of a microorganism which cause differences to be made in bacterial growth, and production and types of the secondary metabolite depending on combination and a composition ratio thereof.

Therefore, during an attempt to find an environmentally friendly natural product-derived herbicide and a method for mass producing the same, the present inventors have completed the present invention by verifying that: a novel *Streptomyces scopuliridis* KR-001 strain, a culture broth thereof, or a fraction of the culture shows the weed-killing ability on grass weeds, broad leaf weeds, and hard to control weeds; and that an optimal condition to reduce the unit cost of production is established by selecting a carbon source and a nitrogen source which increase yield of the active material produced by the strain so that it has been found that the strain can be usefully applied for mass production of a natural substance-derived weed control material.

SUMMARY OF THE INVENTION

One object of the present invention is to provide a novel *Streptomyces scopuliridis* strain.

Another object of the present invention is to provide a herbicide composition for weed control, and a method for controlling weeds by using the composition, the composition containing, as an active ingredient, any one or more selected from the group consisting of the strain, culture broth thereof, an extract of the culture broth, a fraction of the culture broth or extract, and an active fraction of the fraction.

Still another object of the present invention is to provide a medium composition for mass production of a *Streptomyces scopuliridis* strain and a method for mass producing the *Streptomyces scopuliridis* strain, wherein, the composition containing, as an active ingredient, potato starch and soybean powder.

In order to achieve the objects, the present invention provides a *Streptomyces scopuliridis* KR-001 strain deposited under accession number KCTC 12156BP.

The present invention also provides a herbicide composition for weed control containing, as an active ingredient, any one or more selected from the group consisting of the *Streptomyces scopuliridis* KR-001 strain deposited under accession number KCTC 12156BP, culture broth thereof, an extract of the culture broth, a fraction of the culture broth or extract, and an active fraction of the fraction.

Furthermore, the present invention provides a method for weed control including treating a weed, or a seed or a habitat thereof with any one or more selected from the group consisting of the *Streptomyces scopuliridis* KR-001 strain deposited under accession number KCTC 12156BP, culture broth thereof, an extract of the culture broth, a fraction of the culture broth or extract, and an active fraction of the fraction.

The present invention also provides a medium composition for mass production of a *Streptomyces scopuliridis* strain, the composition containing potato starch and soybean powder as active ingredients.

Furthermore, the present invention provides a method for mass producing a *Streptomyces scopuliridis* strain including:

1) preparing a medium composition containing potato starch and soybean powder as active ingredients; and 2) inoculating the medium composition of step 1) with 1 to 3% (w/v) of the *Streptomyces scopuliridis* strain, and then culturing for 5 to 7 days.

The present invention also provides the *Streptomyces scopuliridis* KR-001 strain deposited under accession number KCTC 12156BP, culture broth thereof, an extract of the culture broth, a fraction of the culture broth or extract, and a use of the fraction.

Furthermore, the present invention provides a use of a medium for a *Streptomyces scopuliridis* strain including potato starch and soybean powder to be used as a medium composition for mass production.

According to the present invention, since the *Streptomyces scopuliridis* KR-001 strain deposited under accession number KCTC 12156BP, a culture broth thereof, or a fraction of the culture shows an excellent weed-killing ability on grass weeds, broad leaf weeds, and hard-to control weeds, and also the medium composition containing an optimal condition of a carbon source and a nitrogen source significantly increases yield of an active material produced by the strain with low-cost, the strain can be usefully employed to a composition for weed control or a method for weed control.

BRIEF DESCRIPTION OF THE DRAWINGS

The above and other objects, features and other advantages of the present invention will be more clearly understood from the following detailed description taken in conjunction with the accompanying drawings, in which.

Hexane Fr.: Hexane fraction;
EtOAc Fr.: Ethyl acetate fraction;
BuOH Fr.: Butanol fraction;
AQ Fr: Water fraction; and
CK: Negative control.

Figure 4:
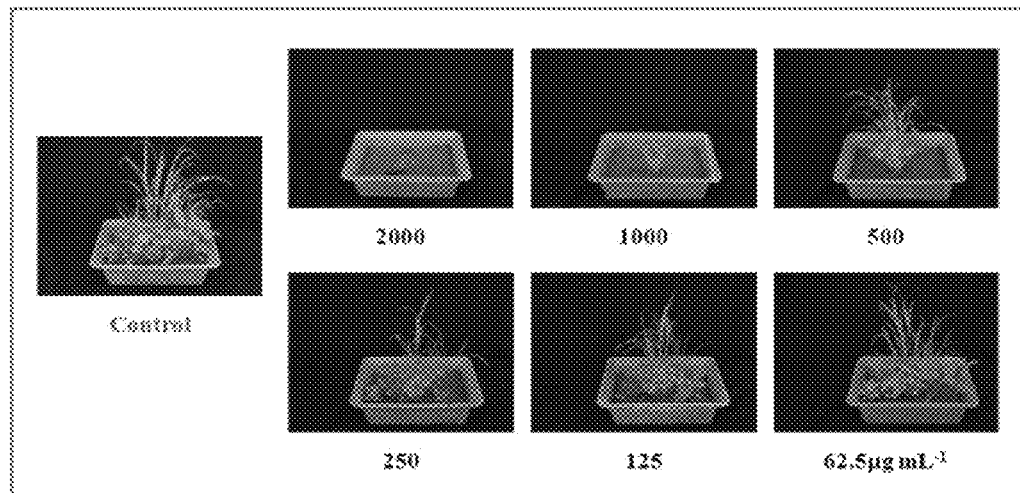

FIG. 4 is an image showing a weed-killing effect of an ethyl acetate fraction of culture broth of the strain of the present invention for each concentration after soil treatment.

Figure 5:
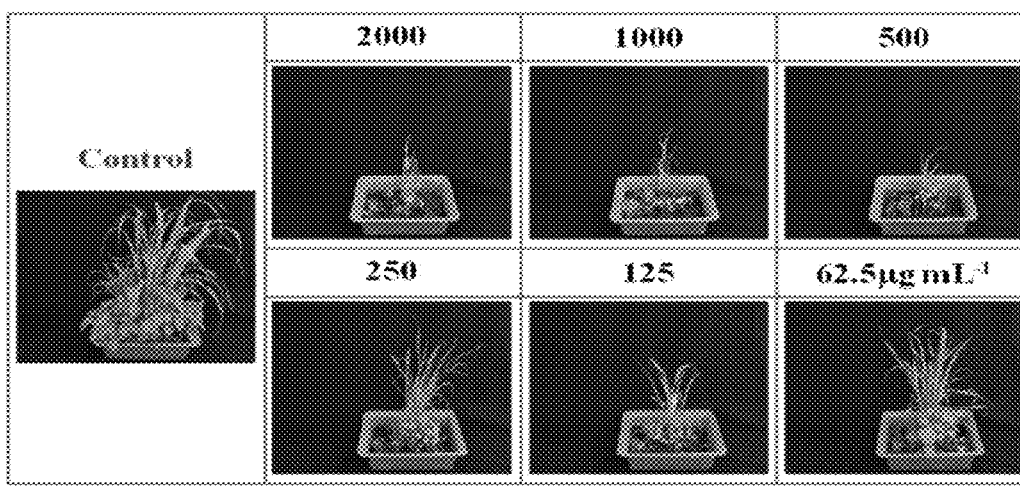

FIG. 5 is an image showing a weed-killing activity of the ethyl acetate fraction of culture broth of the strain of the present invention for each concentration after foliage treatment.

Figure 6:
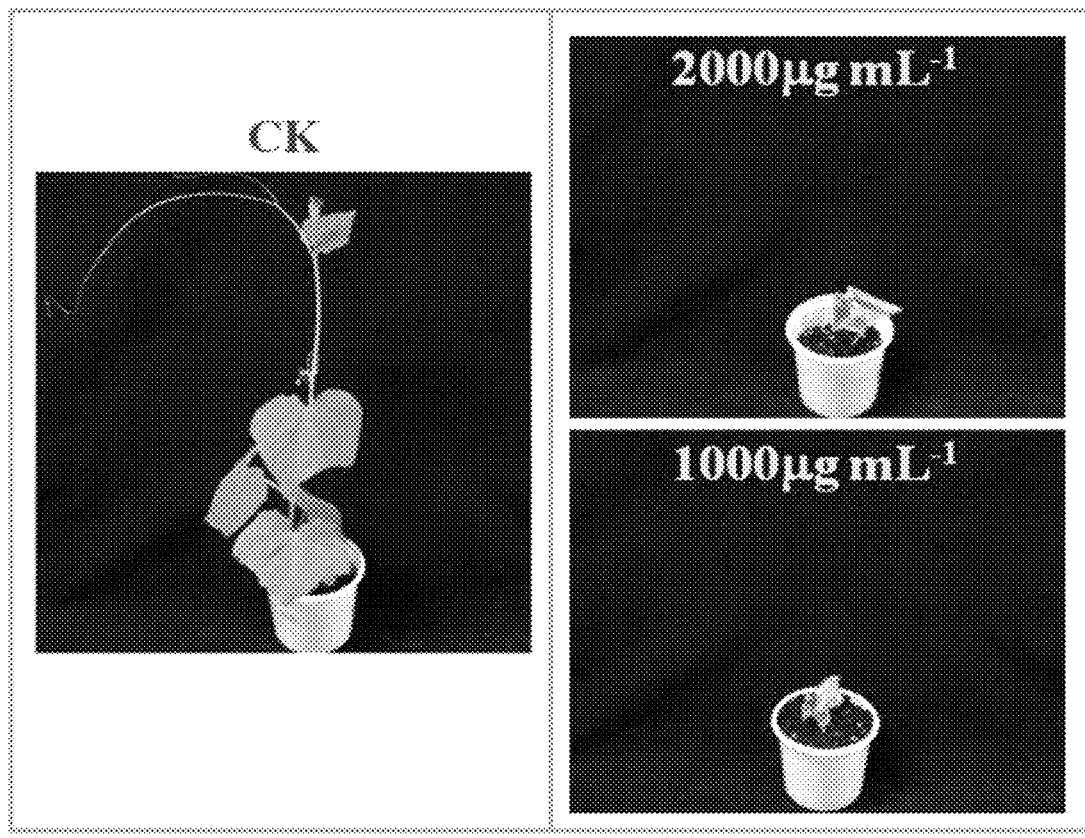

FIG. 6 is an image showing a weed control effect, on *Sciyos angulates*, of the ethyl acetate fraction of culture broth of the strain of the present invention for each concentration under the greenhouse condition after foliage treatment.

Figure 7:
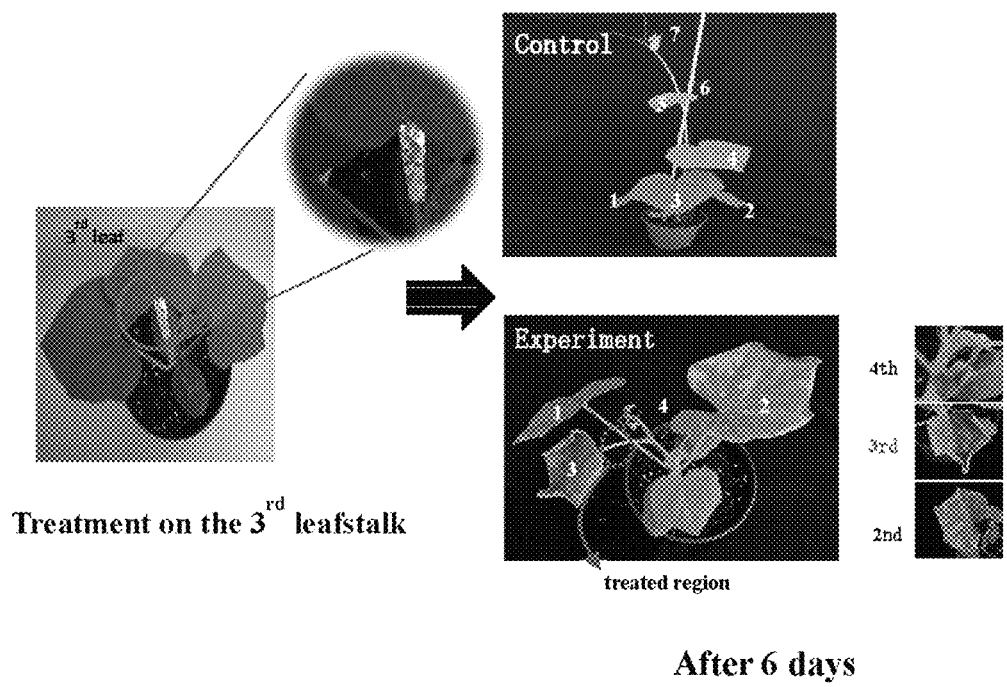

FIG. 7 is an image showing a *Sciyos angulatus* control effect of the ethyl acetate fraction of culture broth of the strain of the present invention through transition into a body under the greenhouse condition.

Figure 8:
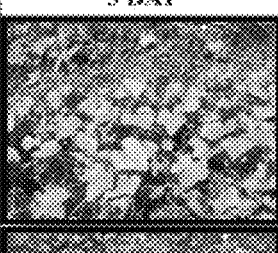

FIG. 8 is an image showing a weed control effect, on *Sciyos angulatus*, of the ethyl acetate fraction of culture broth of the strain of the present invention under a field condition after foliage treatment.

Figure 9:
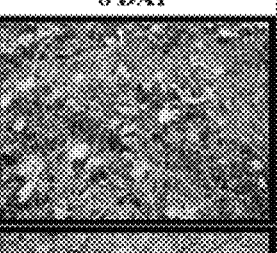

FIG. 9 is an image showing a weed control effect, on *Humulus japonicus* Sieb. & Zucc., of the ethyl acetate fraction of culture broth of the strain of the present invention under the field condition for each concentration, and time after treatment of the fraction.

Figure 10:
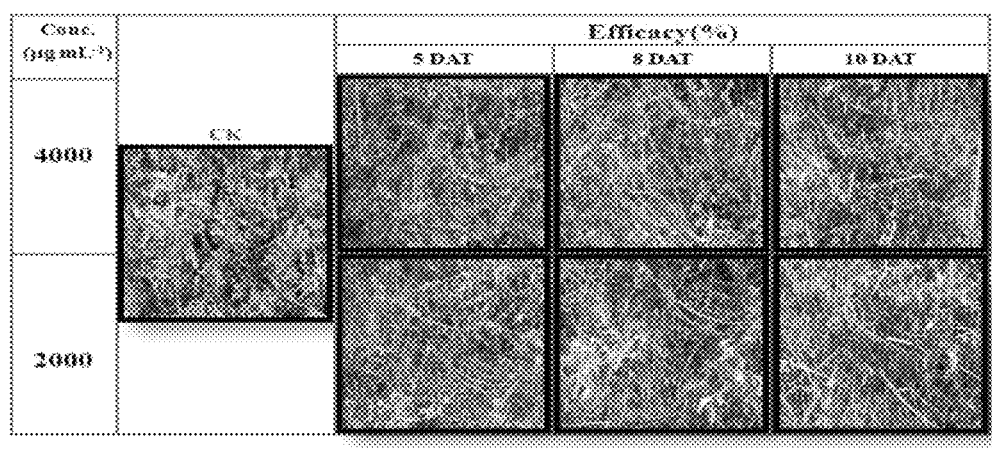

FIG. 10 is an image showing a weed control effect, on *Artemisia princes Pampan*, of the ethyl acetate fraction of culture broth of the strain of the present invention under the field condition after foliage treatment for each concentration, and time after treatment of the fraction.

Figure 11:
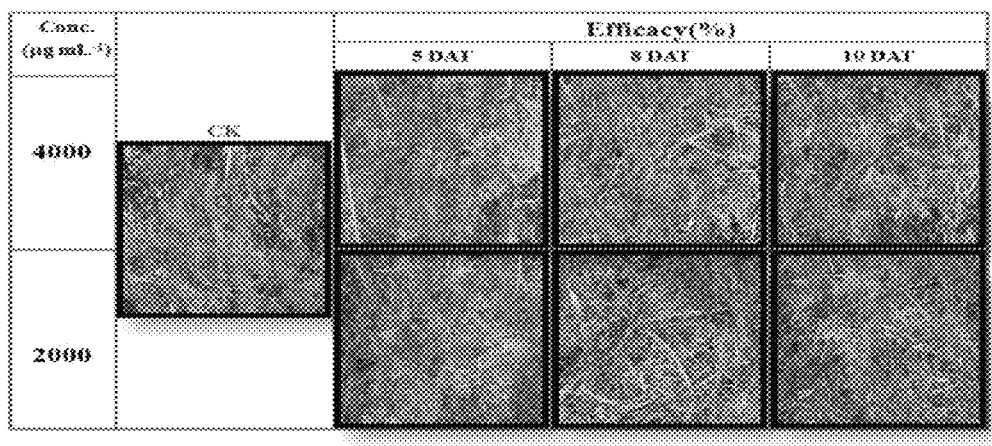

FIG. 11 is an image showing a weed control effect, on *Equisetum arvense* L., of the ethyl acetate fraction of culture broth of the strain of the present invention under the field condition after foliage treatment for each concentration, and time after treatment of the fraction.

Figure 12:

FIG. 12 is an image showing a weed control effect, on *Trifolium repens* L., of the ethyl acetate fraction of culture broth of the strain of the present invention under the field condition after foliage treatment for each concentration, and time after treatment of the fraction.

Figure 13:
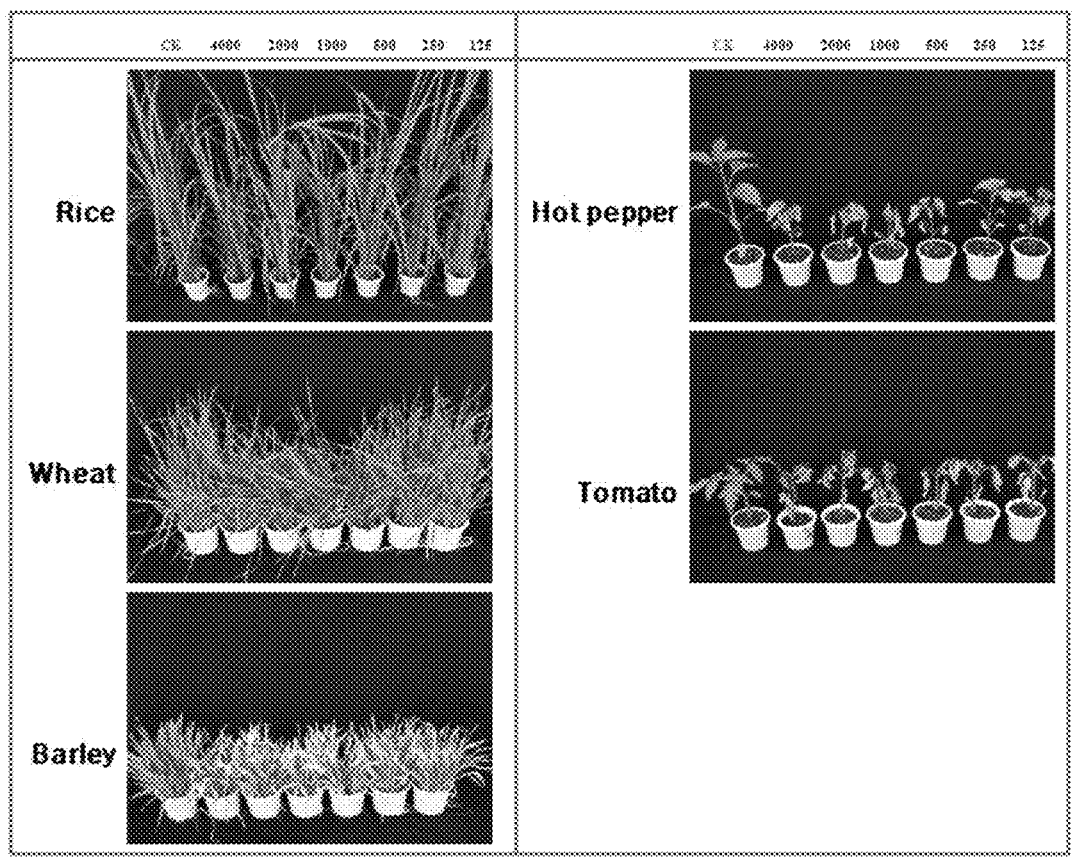

FIG. 13 is an image showing phytotoxicity due to the ethyl acetate fraction of culture broth of the strain of the present invention under the greenhouse condition on three types of grass crops, which are rice, wheat, and barley, and two types of broad leaf weeds which are hot peppers, and tomatoes.

FIG. 14 is an image comparing weed-killing abilities of the ethyl acetate fraction of culture broth of the strain of the present invention (EA fr.), bialaphos and glufosinate for each concentration after foliage treatment.

Figure 15:
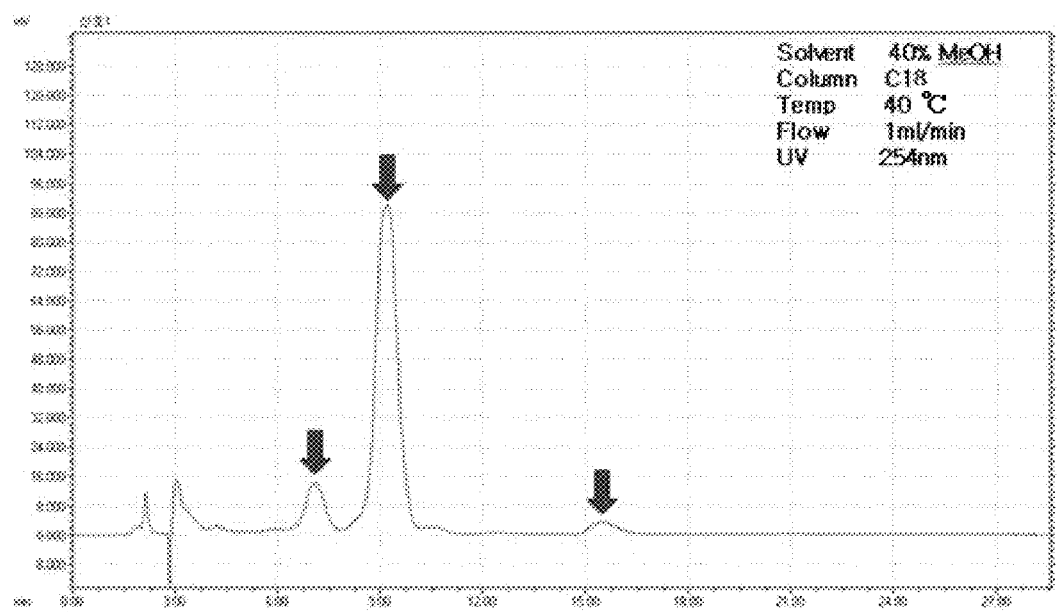

FIG. 15 shows a graph of a HPLC result of the ethyl acetate fraction of culture broth of the strain of the present invention.

Figure 16:
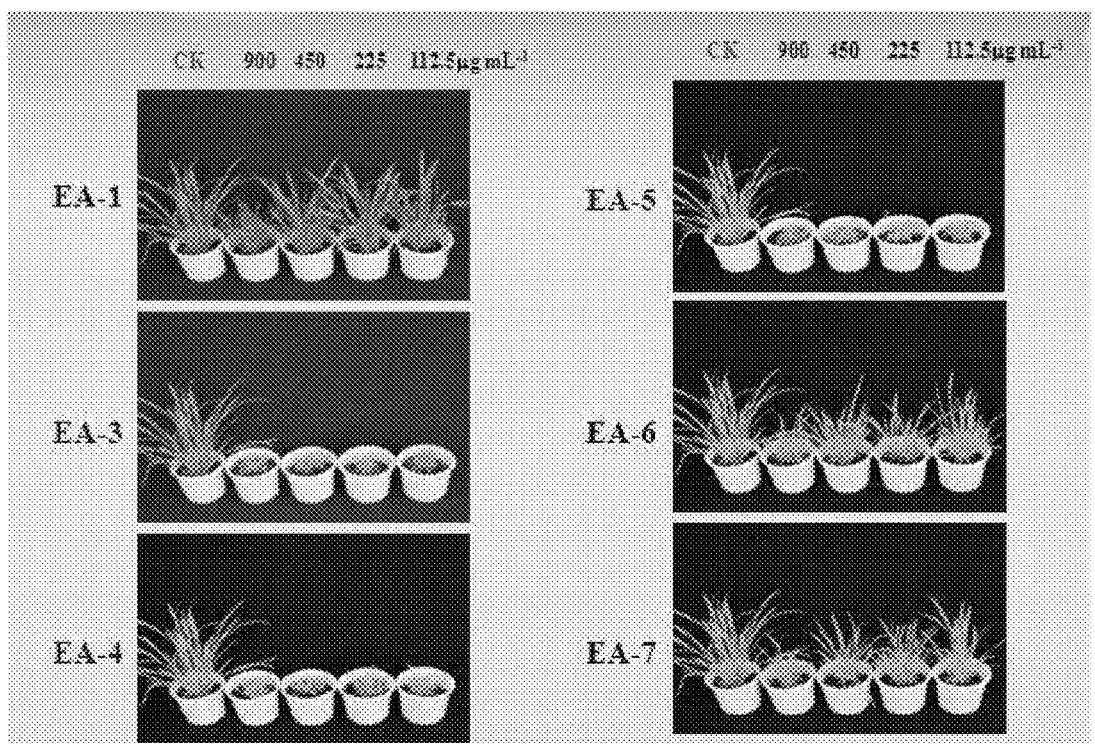

FIG. 16 is an image showing weed-killing abilities of active material fractions of the ethyl acetate of the strain of the present invention (EA-1, EA-3, EA-4, EA-5, EA-6 and EA-7; EA: Ethyl acetate fraction).

Figure 17:
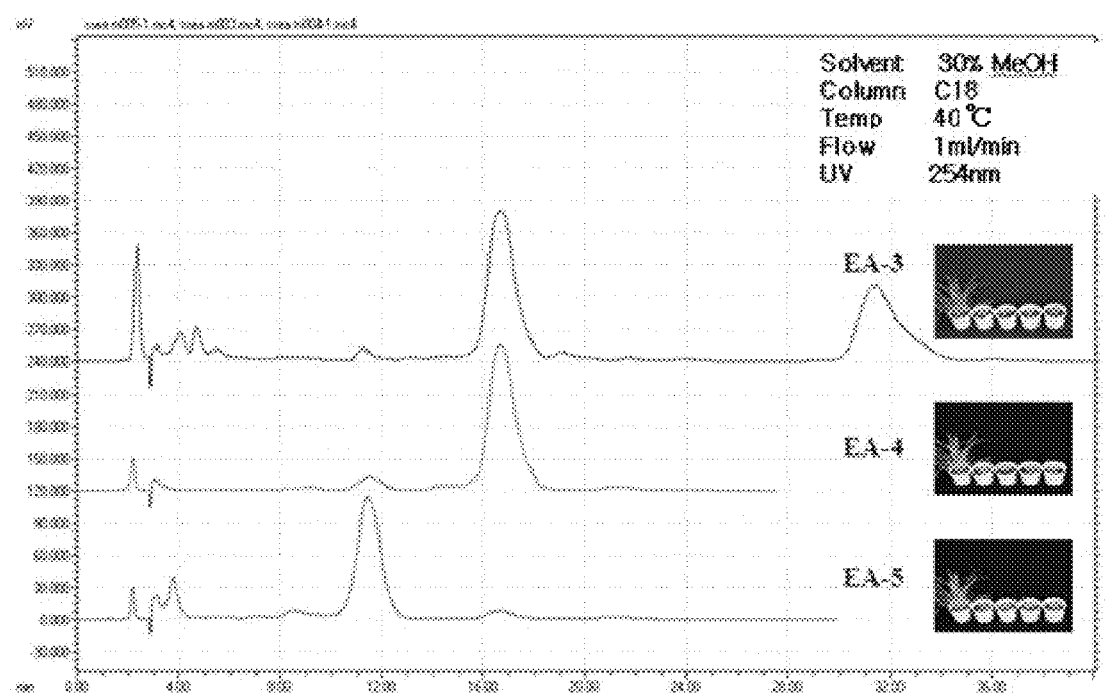

FIG. 17 is a graph showing weed-killing abilities of EA-3, EA-4 and EA-5 after foliage treatment, wherein the graph is obtained by performing HPLC on the ethyl acetate fraction of culture broth of the strain of the present invention.

Figure 18:
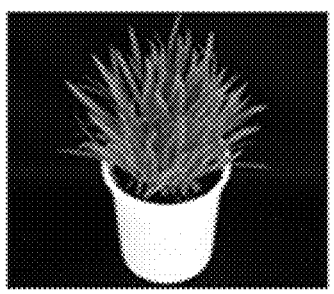
Figure 18:
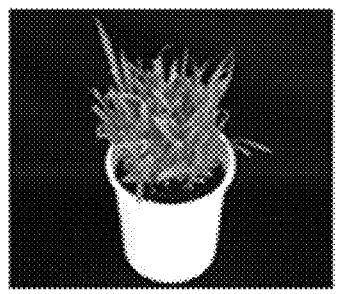
Figure 18:
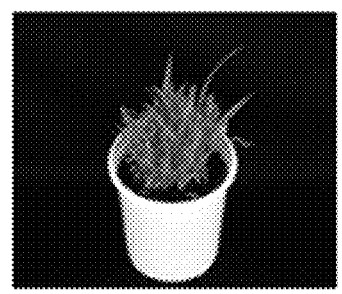
Figure 18:
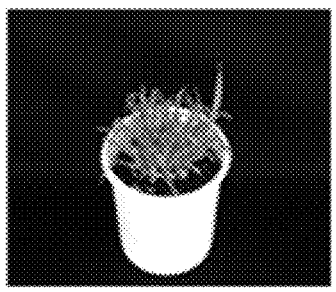
Figure 18:
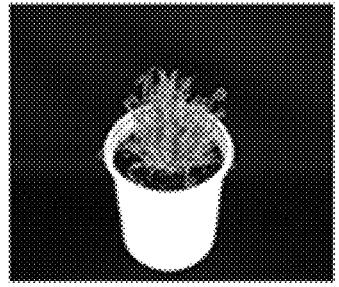
Figure 18:
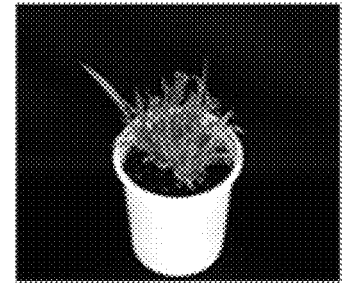

FIG. 18 is an image showing a weed-killing activity of culture filtrate of the *Streptomyces scopuliridis* KR-001 strain depending on a type of carbon sources.

Figure 19:
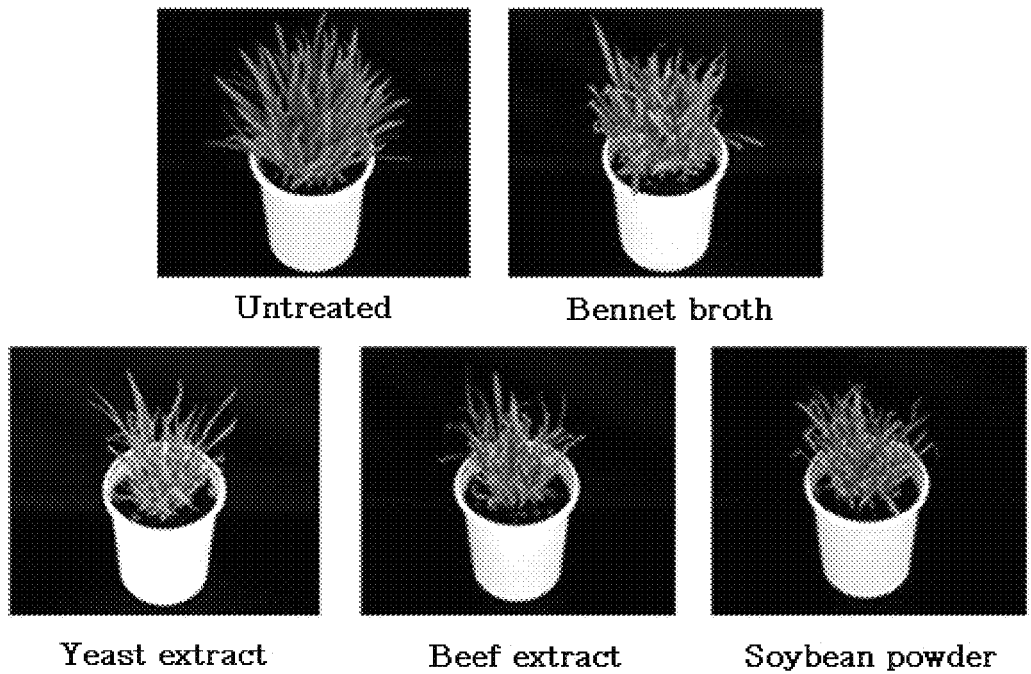

FIG. 19 is an image showing the weed-killing activity of culture filtrate of the *Streptomyces scopuliridis* KR-001 strain depending on a type of nitrogen sources.

Figure 20:
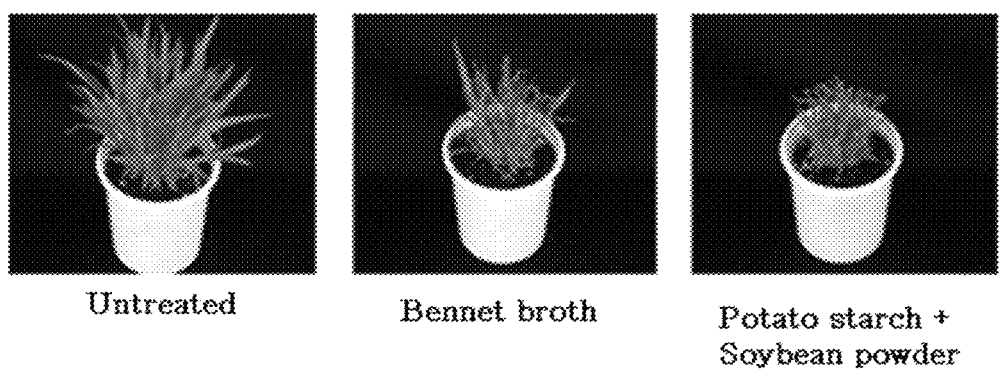

FIG. 20 is an image showing the weed-killing activity of culture filtrate of the *Streptomyces scopuliridis* KR-001 strain according to combination of carbon sources and nitrogen sources.

Figure 21:
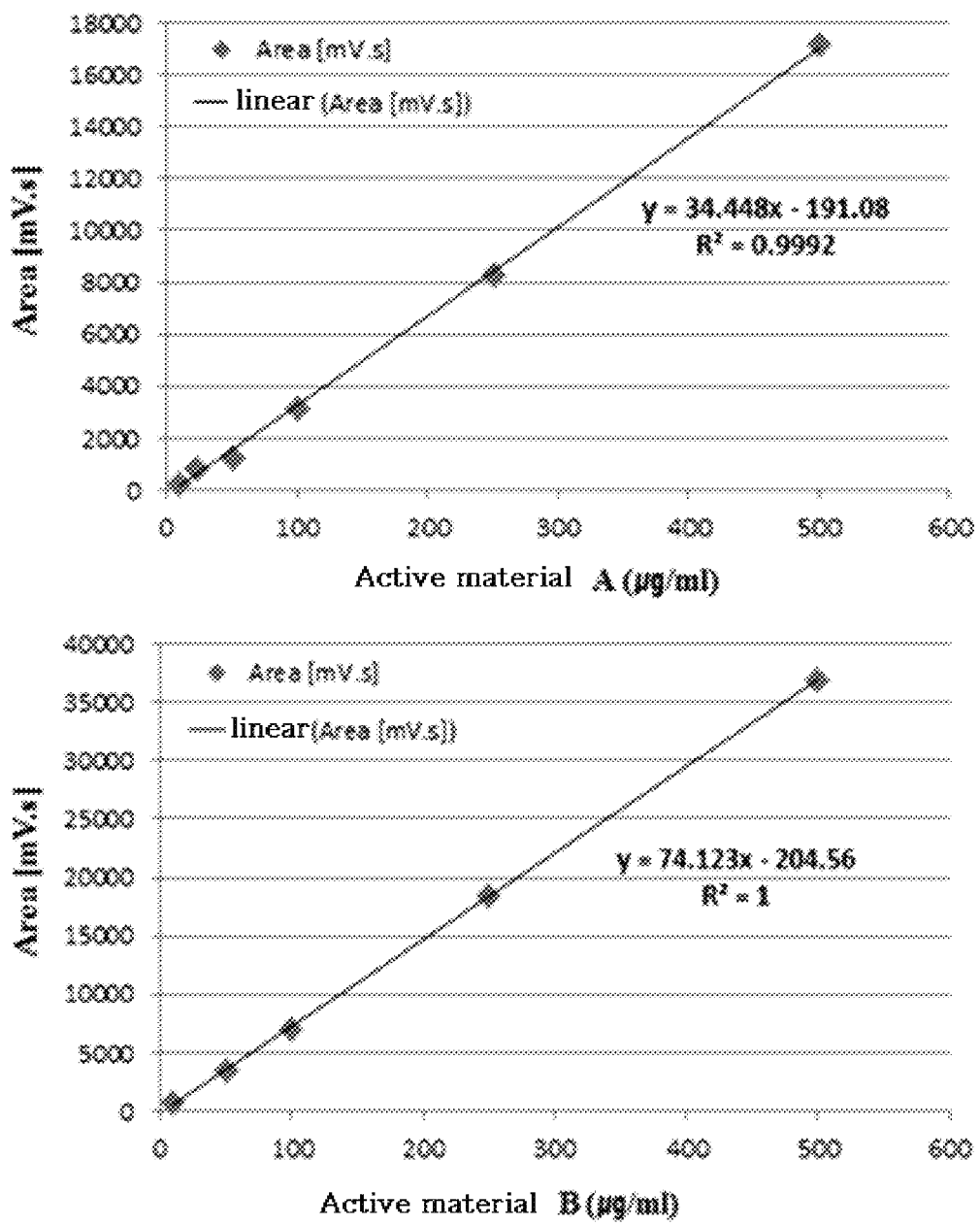

FIG. 21 are normalized graphs of quantifying materials A (upper side) and B (bottom side) which have a weed-killing activity, and are produced by the *Streptomyces scopuliridis* KR-001.

Figure 22:
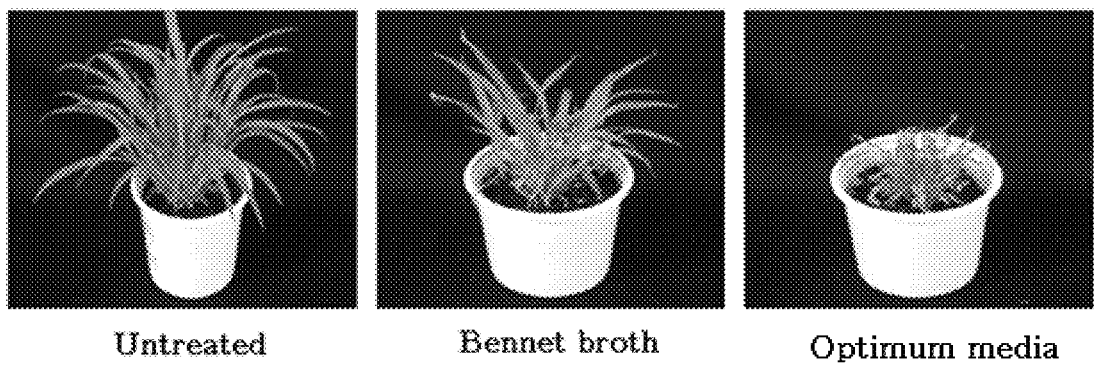

FIG. 22 is an image showing a weed-killing activity of an optimal culture medium of the *Streptomyces scopuliridis* KR-001 strain.

DESCRIPTION OF THE PREFERRED EMBODIMENTS

Hereinafter, the term used herein will be described in detail.

As used herein, the term "mass production" means that the number of bacteria of *Streptomyces scopuliridis* is significantly expanded, proliferated, increased, or enhanced than that of those cultured in the conventional medium (e.g., Bennett's medium) used to culture *Streptomyces scopuliridis* in the art, and preferably means that the number of bacteria is expanded, proliferated, or enhanced by at least two times.

As used herein, the term "*Streptomyces scopuliridis* medium composition" means a *Streptomyces scopuliridis* medium, a composition for culturing *Streptomyces scopuliridis*, or a composition added to the *Streptomyces scopuliridis* medium.

Hereinafter, the present invention will be described in more detail.

The present invention provides a *Streptomyces scopuliridis* KR-001 strain deposited under accession number KCTC 12156BP.

A strain, which was obtained from forest soil around Daecheongho, Chungown-gun, Chungcheongbuk-do by Korea Research Institute of Bioscience and Biotechnology (KRIBB) through isolation and culture, and freeze-dried and stored at −70 in a deep freezer, was distributed and then used as a *Streptomyces scopuliridis* KR-001 strain (hereinafter, referred to as KR-001 strain) according to the present invention.

The KR-001 strain is identified as a novel strain having about 99.7% of homology with *Streptomyces scopuliridis* RB72T through a 16s rRNA gene homology analysis, and classified into *Streptomyces scopuliridis*.

The present inventors named the novel strain as *Streptomyces scopuliridis* KR-001, and deposit the strain to Korean Collection for Type Cultures (KCTC) on Mar. 9, 2012 under accession number KCTC 12156BP.

The present invention also provides a herbicide composition for weed control containing, as an active ingredient, any one or more selected from the group consisting of the *Streptomyces scopuliridis* KR-001 strain deposited under accession number KCTC 12156BP, culture broth thereof, an extract of the culture broth, a fraction of the culture broth or extract, and an active fraction of the fraction.

The extract of culture broth of the strain may be obtained through extraction with an organic solvent. Preferably, extraction may be performed by using an organic solvent alone or by subsequently using two or more of organic solvents, wherein the organic solvent is selected from the group consisting of $C_1$ to $C_4$ alcohol (e.g., methanol, ethanol, propanol, and butanol, etc.), hexane, and ethyl acetate.

The fraction of the extract or culture broth is, preferably, subsequently fractionated by using hexane, ethyl acetate, butanol, and water, but not limited thereto.

The active fraction is preferably a fraction eluted at 6 to 7 min, 8 to 10 min, or 15 to 20 min from column chromatography of the fraction of the culture broth or extract by using methanol, ethanol, or aqueous solutions thereof as a solvent, but not limited thereto.

The weed is preferably any one selected from the group consisting of grass weeds, broad leaf weeds, and hard-to control weeds, but not limited thereto.

The grass weed is preferably any one selected from the group consisting of *Digotaris sanguinalis, Sorghum bicolor, Agropyron smithii* and *Echinochloa crus-galli*, but not limited thereto.

The broad leaf weed is preferably any one selected from the group consisting of *Solanum nigrum, Aeschynomeme indica, Abutilon avicennae, Xanthium strumarium* and *Calystegia japonica*, but not limited thereto.

The hard-to control weed is preferably any one selected from the group consisting of *Sicyos angulates, Humulus japonicus, Artemisia princes, Equisetum arvense* and *Trifolium repens*, but not limited thereto.

The active fraction of the culture broth, an extract thereof, a fraction of the culture broth or extract, or the fraction is preferably any one or more selected from the group consisting of herbicidin A, herbicidin B and herbicidin F, but not limited thereto.

The herbicide composition for weed control may include a carrier and/or diluting agent. As used herein, the term "carrier" means a non-active, organic or inorganic material having an active ingredient, wherein the carrier is mixed or made to facilitate application, storage, transport and/or handing of the active ingredient into a plant or other subjects to be treated. Examples of the diluting agent or carrier include, but not limited to, water, milk, ethanol, mineral oil, and glycerol.

Figure 2:
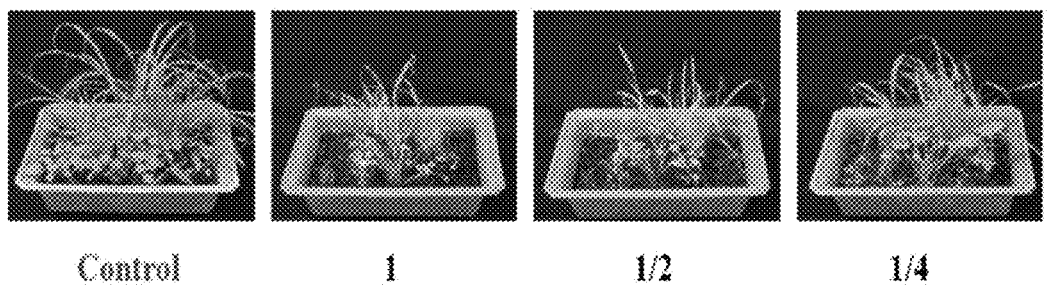
FIG. 2 is an image showing a weed-killing activity of culture broth of the strain of the present invention for each concentration after foliage treatment.

The present inventors have proven an excellent weed-killing activity, on three types of grass weeds and five types of broad leaf weeds, of culture broth of the KR-001 strain for each concentration after foliage treatment (see Table 3 and FIG. 2).

Figure 3:
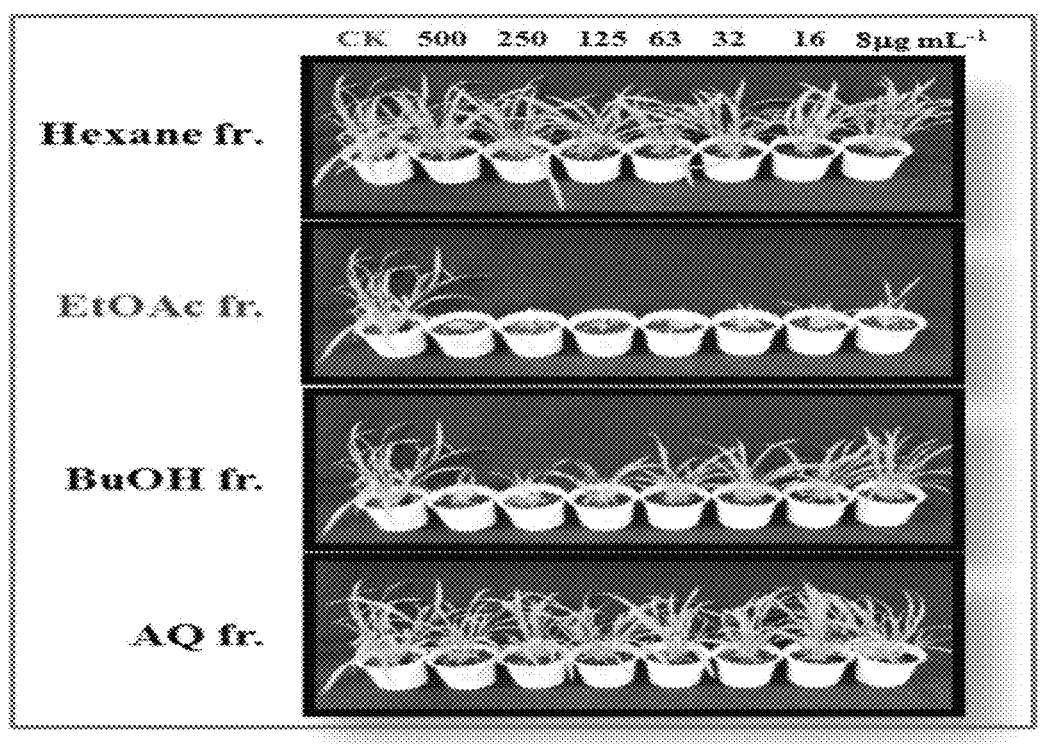
FIG. 3 is an image showing a weed-killing activity, on *Digotaris sanguinalis*, of each fraction of culture broth of the strain of the present invention (i.e. hexane, ethyl acetate, butanol, and water fractions) for each concentration after foliage treatment.

The present inventors have proven that when the culture broth are fractionated into hexane, ethyl acetate, butanol, and water layers, and then four types of grass weeds and five types of broad leaf weeds are treated with each solvent fraction for each concentration through foliage treatment, an excellent weed-killing activity is exhibited in the ethyl acetate fraction and butanol fraction (see Table 4 and FIG. 3).

The present inventors have proven a weed-killing ability of the ethyl acetate fraction after foliage treatment and soil treatment on four types of grass weeds and five types of broad leaf weeds for each concentration (see Tables 5 and 6, and FIGS. 4 and 5).

The present inventors have proven that the ethyl acetate fractions having concentrations of 2000 µg mL$^{-1}$ and 1000 µg mL$^1$ are completely control *Sicyos angulatus* after foliage treatment under a greenhouse condition (see FIG. 6).

The present inventors have proven that the ethyl acetate fraction has a *Sicyos angulatus* control effect under the greenhouse condition through transition to the body (see FIG. 7).

The present inventors have proven that the ethyl acetate fraction has an excellent weed-killing ability after foliage treatment for each concentration on *Sicyos angulatus* under a field condition, and that the weed-killing ability increases with the lapse of time which indicates excellent efficacy durability (see Table 7 and FIG. 8).

The present inventors have proven that the ethyl acetate fraction has an excellent ability to kill hard-to-control weeds, for example, *umulus japonicus, Artemisia princes,* *Equisetum arvense* and *Trifolium repens* after foliage treatment under the field condition (see Table 8, FIGS. 9, 10, 11 and 12).

The present inventors have proven that when grass crops (such as rice, wheat, and barley), and broad leaf crops (such as hot peppers, and tomatoes) are treated with the ethyl acetate fraction through foliage treatment, phytotoxicity are induced in all five subject corps, indicating that there is no crop-selectivity (see Table 9 and FIG. 13).

The present inventors have proven that when weed-killing abilities of ethyl acetate fraction, bialapos, and glufosinate in the same concentration are cross compared after foliage treatment, the ethyl acetate fraction has a weed-killing ability on a level of bialapos, and glufosinate (see FIG. 14).

The present inventors detect an active material of the ethyl acetate fraction as a fraction which is eluted from column chromatography by using methanol, ethanol, or aqueous solutions thereof as a solvent (see FIG. 15). Herbicidine A, herbicidine B and herbicidine F are isolated from the detected fraction. In addition, it has been proven that the detected fraction, i.e., the active fraction has an excellent weed-killing ability (see FIGS. 16 and 17).

Therefore, the *Streptomyces scopuliridis* KR-001 strain deposited under accession number KCTC 12156BP, culture broth thereof, an extract of the culture broth, a fraction of the culture broth or extract, and an active fraction of the fraction show excellent weed-killing ability on grass weeds, broad leaf weeds, and hard-to-control weeds, thereby being usefully employed as an active ingredient of a herbicide composition for weed-control.

Further, the present invention provides a method for weed control including: treating a weed or a seed or a habitat thereof with any one or more selected from the group consisting of the *Streptomyces scopuliridis* KR-001 strain deposited under accession number KCTC 12156BP, culture broth thereof, an extract of the culture broth, a fraction of the culture broth or extract, and an active fraction of the fraction.

The present inventors may treat foliage of a plant or soil with the culture broth, the each solvent fraction, and the ethyl acetate fraction. The culture broth, the each solvent fraction, and the ethyl acetate fraction may be in a form of powder, coarse dust, micro granules, granules, wettable powder, emulsifiable concentrate, liquid vehicle, suspension concentrates, water degradable granules, or oil suspension. It has been proven that the culture broth, the each solvent fraction, and the ethyl acetate fraction have an excellent weed-killing ability on grass weeds, broad leaf weed, and hard-to control weeds after soil treatment for treating soil, and foliage treatment for directly spraying to stems and leaves of plants.

Therefore, the *Streptomyces scopuliridis* KR-001 strain deposited under accession number KCTC 12156BP of the present invention, culture broth thereof, an extract of the culture broth, a fraction of the culture broth or extract, and an active fraction of the fraction show the excellent weed-killing ability after foliage treatment or soil treatment, thereby being usefully employed to a method for controlling weed by treating weeds, a seed thereof, or a habitat thereof.

The present invention also provides a medium composition for mass production of a *Streptomyces scopuliridis* strain, the composition containing potato starch and soybean powder as active ingredients.

Preferably, the potato starch is contained in 1 to 3% (w/v), and soybean powder is contained in 0.5 to 2% (w/v), and more preferably, the potato starch is contained in 3% (w/v), and soybean powder is contained in 2% (w/v).

Preferably, the *Streptomyces scopuliridis* strain is a *Streptomyces scopuliridis* KR-001 strain deposited under accession number KCTC 12156BP, but not limited thereto.

Preferably, the composition further includes glucose, but not limited thereto.

Preferably, the composition contains 1% (w/v) of potato starch, 1% (w/v) of glucose and 1% (w/v) soybean powder, but not limited thereto.

In a specific example of the present invention, to select a carbon source suitable for microorganism growth and production of a material having a weed-killing activity for a culture medium of the *Streptomyces scopuliridis* KR-001 strain, the present inventors have proven that as a result of measuring final pH, microorganism growing degrees, and weed-killing activities of control culture filtrate, in which the conventional Bennett's medium is inoculated with culture broth including precultured *Streptomyces scopuliridis*, and of culture filtrate obtained by adding glucose, sucrose, soluble starch, potato starch, corn starch, maltose, and molasses, which are carbon sources, to a minimal nutrient medium including soy peptone, and then inoculating the medium with culture broth including the pre-cultured strain, when compared with control culture broth, the culture broth including potato starch, corn starch, and maltose added thereto show a very good bacterial growth, and about 70% of the weed-killing activity, and also that an amount of the produced active material is the largest when pH of culture filtrate is around 5 to 7 (see Table 11 and FIG. 18).

Moreover, to select a nitrogen source suitable for microorganism growth and production of a material having a weed-killing activity, the present inventors have proven that as a result of measuring final pH, growth of microorganism, and weed-killing activities of control culture filtrate, and of culture filtrate obtained by adding skim milk, tryptone, a beef extract, peptone, corn steep liquor (CSL), soybean powder, casein peptone, or a yeast extract, which are nitrogen sources, to a basal medium including glycerol, and then inoculating the medium with culture broth including precultured *Streptomyces scopuliridis*, when compared with control culture broth, the culture broth including the yeast extract and beef extract added thereto show a favorable bacterial growth, 40 to 50% of the weed-killing activity, and final pH fallen within a range of 6 to 7. It has been also proven that although culture broth including the added soybean powder shows a normal range of microbial growth, a weed-killing activity thereof is excellent (see Table 12 and FIG. 19).

In addition, to select a carbon source and a nitrogen source in a ratio suitable for microorganism growth and production of a material having a weed-killing activity for culture medium of the *Streptomyces scopuliridis* KR-001 strain, the present inventors have proven that: as a result of measuring final pH, microorganism growth, and weed-killing activities of control culture filtrate, and of culture filtrate obtained by adding potato starch, corn starch, or maltose, which are carbon sources, and adding a beef extract, soybean powder, or a yeast extract, which are nitrogen sources, and then inoculating the resultant with culture broth including pre-cultured *Streptomyces scopuliridis*, in the case where potato starch, as a carbon source, and soybean powder, as a nitrogen source, are used to culture the *Streptomyces scopuliridis* KR-001 strain, bacterial growth is favorable; 90% of the weed-killing activity is exhibited; and final pH is fallen within a range of 5 to 7 (see Table 13 and FIG. 20).

Further, to establish a carbon source and a nitrogen source optimized medium composition suitable for microorganism growth and production of a material having a weed-killing activity for the *Streptomyces scopuliridis* KR-001 strain, the present inventors have proven that as a result of measuring contents of the material having the weed-killing activity of control culture filtrate, culture filtrates obtained by adding 1 to 3% (w/v) potato starch, and 0.5 to 2.0% (w/v) soybean powder, and then inoculating the resultant with culture broth including precultured *Streptomyces scopuliridis*, and culture filtrate obtained by adding 1% (w/v) potato starch, 1% (w/v) glucose, and 1% (w/v) soybean powder, and then inoculating the resultant with culture broth including the precultured strain, in terms of production unit cost and an amount of the produced material having the weed-killing ability, the culture medium including 3% (w/v) potato starch, and 2% (w/v) soybean powder added thereto is the most suitable so that the medium including 3% (w/v) potato starch, and 2% (w/v) soybean powder is an optimal culture medium as a culture medium of the *Streptomyces scopuliridis* KR-001 strain (see Tables 15 and 16, and FIG. 21).

In addition, to evaluate a weed-killing activity of the optimal culture medium of the *Streptomyces scopuliridis* KR-001 strain, the present inventors have proven that when culture broth, in which *Streptomyces scopuliridis* KR-001 strain is cultured by using the optimal medium, is sprayed to *Digotaris sanguinalis* for foliage treatment, culture broth from culture by using the optimal medium shows a strong weed-killing ability (see FIG. 22).

Therefore, the medium composition prepared by mixing a carbon source and a nitrogen source in an optimal condition for mass production of a *Streptomyces scopuliridis* KR-001 strain of the present invention shows excellent microorganism growth, and weed-killing activity and have the production cost-reducing effect, and thus, the medium composition can be usefully employed to mass culture of the *Streptomyces scopuliridis* strain for production of a weed-control agent.

Further, the present invention provides a method for mass producing a *Streptomyces scopuliridis* KR-001 strain by using a medium composition containing potato starch and soybean powder as active ingredients.

Provided is a method for mass producing a *Streptomyces scopuliridis* strain including:

1) preparing a medium composition containing potato starch and soybean powder as active ingredients; and 2) inoculating the medium composition of step 1) with 1 to 3% (w/v) of the *Streptomyces scopuliridis* KR-001 strain, and then culturing for 5 to 7 days.

Preferably, the medium composition in step 1) further includes glucose, but not limited thereto.

Preferably, the medium composition in step 1) contains 1 to 3% (w/v) potato starch and 0.5 to 2% (w/v) of soybean powder, but not limited thereto.

Preferably, after the medium composition in step 1) is inoculated with the *Streptomyces scopuliridis* KR-001 strain, the resultant is cultured for 5 to 7 days with 150 to 300 rpm at 25 to 30, and more preferably, the resultant is culture for 5 days with 170 rpm at 27.

Preferably, the *Streptomyces scopuliridis* strain is a *Streptomyces scopuliridis* KR-001 strain deposited under accession number KCTC 12156BP, but not limited thereto.

Therefore, culture broth of the *Streptomyces scopuliridis* strain produced by using the medium composition containing potato starch and soybean powder as active ingredients of the present invention shows excellent microorganism growth, an excellent weed-killing activity and production cost-reducing effect, and thus, the culture broth can be usefully employed to mass culture of the *Streptomyces scopuliridis* strain for production of a weed-control agent.

The present invention also provides the *Streptomyces scopuliridis* KR-001 strain deposited under accession number KCTC 12156BP, culture broth thereof, an extract of the culture broth, a fraction of the culture broth or extract, and a use of the fraction as a herbicide composition for weed control.

Therefore, the *Streptomyces scopuliridis* KR-001 strain deposited under accession number KCTC 12156BP of the present invention, culture broth thereof, an extract of the culture broth, a fraction of the culture broth or extract, and an active fraction of the fraction show an excellent weed-killing ability on grass weeds, broad leaf weeds, and hard-to-control weeds, and thus, the present invention can be usefully employed as an active ingredient of a herbicide composition for weed control.

Further, the present invention provides a use of a medium of a *Streptomyces scopuliridis* strain including potato starch and soybean powder as active ingredients to be used as a medium composition for mass production.

Therefore, the *Streptomyces scopuliridis* KR-001 strain deposited under accession number KCTC 12156BP of the present invention, culture broth thereof, an extract of the culture broth, a fraction of the culture broth or extract, and an active fraction of the fraction show an excellent weed-killing ability on grass weeds, broad leaf weeds, and hard-to-control weeds, and thus, the present invention can be usefully employed as an active ingredient of a herbicide composition for weed-control.

Hereinafter, the present invention will be described in detail.

However, following examples are only to specifically illustrate the present invention, and the content of the invention is not limited thereto.

Example 1

Isolation of Strain

A strain was isolated from forest soil around Daecheon-gho, Chungown-gun, Chungcheongbuk-do. An agar (including Humic acid-vitamin) medium was used, and an appropriate concentration of cyclohexamide or nalidixic acid was added and used to inhibit growth of bacteria and fungi. A soil sample, 1 g per each, was added to 10 ml of a sterilized saline solution and sufficiently mixed through a vortex. Then, 100 ul of each sample was spread on an isolation medium, and cultured and observed for certain time at 28. A culture condition was periodically observed during a period of culture, and the cultured colony was inoculated to a new medium to isolate a single colony. Then, selection was performed through a microscopic observance. The isolation medium and culture condition of *actinomyces* are as follows (Table 1).

Each isolated strain was cultured on an agar medium. Thereafter, bacterial cells were collected, suspended in 20% sterilized glycerol, and stored in a deep freezer of −70. In addition, for long-term storage, lyophilization was performed, i.e., each isolated strain was cultured on a solid medium, suspended in 10% sterilized skim milk, lyophilized, and stored at 4 or below.

TABLE 1

Isolation medium and culture condition of *actinomyces*

| Microorganism | Isolation medium and composition | | pH | Temperature of culture | Period of culture |
| --- | --- | --- | --- | --- | --- |
| *Actinomyces* | HV agar (g/l) | | pH 7.2 | 28° C. | 7-30 days |
| | Humic acid | 1 | | | |
| | Na$_2$HPO$_4$ | 0.5 | | | |
| | KCl | 1.71 | | | |
| | MgSO$_4$7H$_2$O | 0.05 | | | |
| | FeSO$_4$7H$_2$O | 0.01 | | | |
| | CaCO$_3$ | 0.02 | | | |
| | Agar | 18 | | | |

Example 2

Identification of Strain

To identify the strain isolated in <Example 1>, 16S rRNA gene sequence analysis was performed.

Specifically, to obtain a sequence of a 16S rRNA gene of the strain, colony PCR was performed. A single colony was picked by using a toothpick, and mixed with PCR-premix (iNtRON Biotechnology, Korea) to amplify the 16S rRNA gene by using 27f and 1492r primers. The amplified PCR product was purified by using Wizard PCR prep kit (Promega, Medison, Wis., USA), and the sequence analysis was performed by Macrogen (Daejeon, Korea). By using BLAST of NCBI, the sequence was compared with those in GenBank database. The sequence was aligned through CLUSTAL W, and phylogenetic tree was constructed by using PHYDIT program version 3.0. The sequence of the 16S rRNA gene of the strain (SEQ ID NO: 1) was analyzed based on the Neighbour-joining algorithm.

Figure 1:
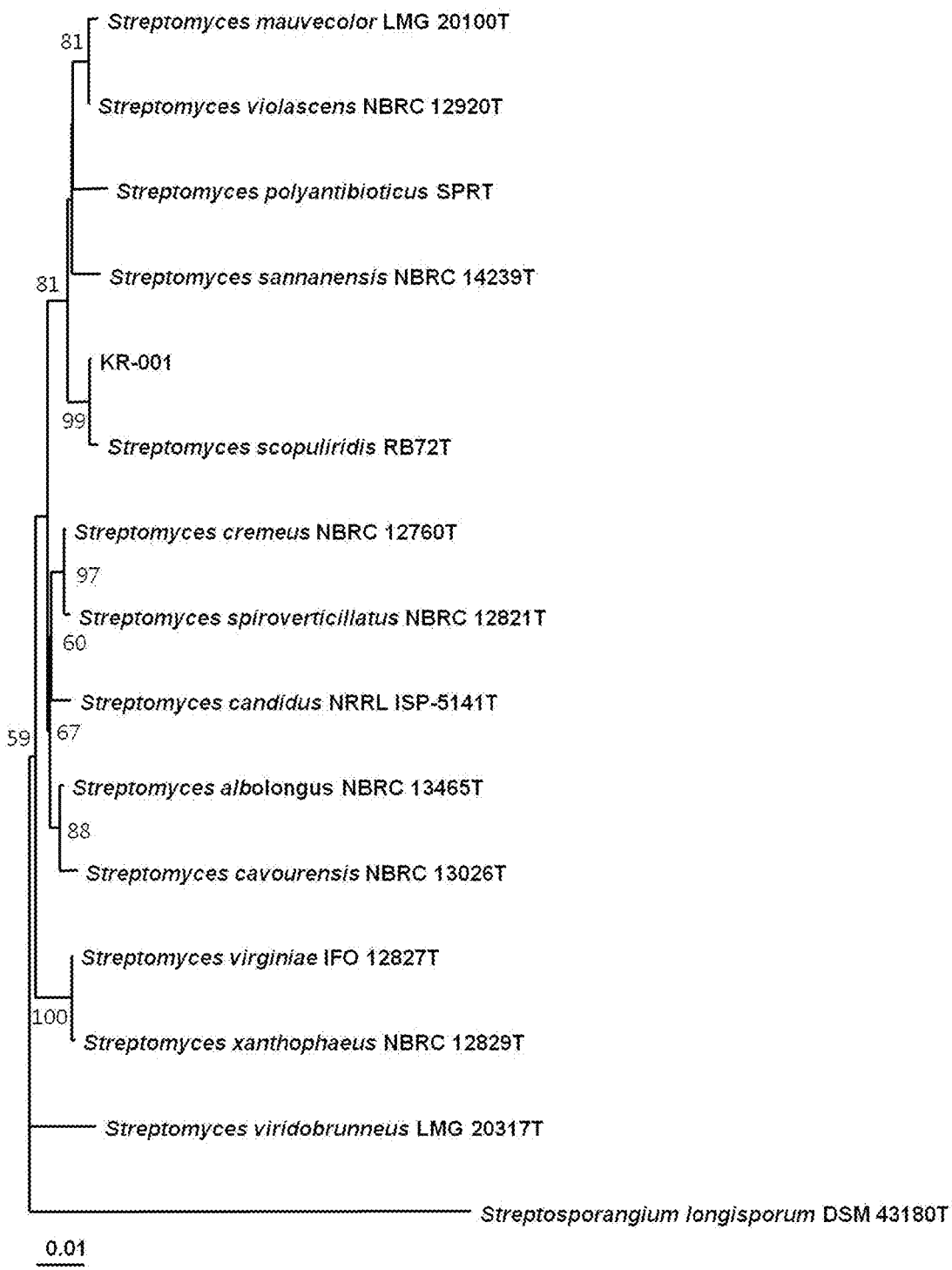
FIG. 1 is a diagram showing a phylogenetic tree based on a 16S rRNA gene sequence of a *Streptomyces scopuliridis* KR-001 strain deposited under accession number KCTC 12156BP.

Consequently, it has been found that the strain is a strain showing 99.7% homology with the *Streptomyces scopuliridis* RB72T (FIG. 1). The strain used in the present invention has been identified as a *Streptomyces scopuliridis* strain, named as *Streptomyces scopuliridis* KR-001, and deposited to Korea Research Institute of Bioscience and Biotechnology (KRIBB) on Mar. 9, 2012, under accession number KCTC 12156BP.

Example 3

Measurement of Activity of Culture Broth of *Streptomyces Scopuliridis* KR-001 Strain for Each Concentration after Foliage Treatment To measure an activity of culture broth of a *Streptomyces scopuliridis* KR-001 strain obtained in <Example 1> after foliage treatment, an experiment was performed by the method below.

Specifically, 500 ml of Bennett's liquid medium was added to a 500 ml baffled flask. Then, the flask was inoculated with 1% of culture broth in which the *Streptomyces scopuliridis* KR-001 strain was precultured. Thereafter, the resultant was cultured for 7 days at 27 with 180 rpm. Then, supernatant of the culture broth was taken and diluted to 1, ½, and ¼ concentration (including Tween-20 0.1%). Foliar treatment was performed to three types of grass weeds (*Digotaris sanguinalis*, *Sorghum bicolor*, and *Echinochloa crus-galli*) and five types of broad leaf weeds (*Solanum nigrum*, *Aeschynomeme indica*, *Abutilon avicennae*, *Xanthium strumarium*, and *Calystegia japonica*) with the resultant in an amount of 14 ml per pot. After five days, a weed-killing ability was evaluated such that an external symptom and efficacy were evaluated through naked eye inspection based on the phytotoxicity index. Compositional components of the Bennett's medium were shown in [Table 2] below.

Consequently, as shown in FIG. 2 and Table 3, a weed-killing ability of the undiluted culture broth on 8 types of weed species was 90% to 100%, and the weed-killing ability at ½ concentration was 70 to 100%. Among subject weeds, the weed-killing abilities on *Digotaris sanguinalis, Solanum nigrum,* and *Aeschynomeme indica* were relatively stronger. With time after treatment of culture broth, the week-killing ability was increased which indicates an efficacy persistent effect. A major symptom was burn-down, and at a concentration of ¼, the color of some grass weed species were turn into purple (Table 3 and FIG. 2).

TABLE 2

Compositional components of bennet medium

| Compositional components | g/L |
|---|---|
| Glucose | 10 |
| Yeast extract | 1 |
| Peptone | 2 |
| Beef extract | 1 |

TABLE 3

Activities of culture broth of *Streptomyces scopuliridis* KR-001 strain on three types of grass weeds (*Digotaris sanguinalis, Sorghum bicolor,* and *Echinochloa crus-galli*) and five types of broad leaf weeds (*Solanum nigrum, Aeschynomeme indica, Abutilon avicennae, Xanthium strumarium,* and *Calystegia japonica*) for each concentration after foliage treatment under greenhouse condition (%)

| Rate | Weed-killing ability (%) | | | | | | | |
|---|---|---|---|---|---|---|---|---|
| (folds) | DIGSA | SORBI | ECGCG | SOLNI | AESIN | ABUTH | XANSI | CAGEH |
| 1 | 100 | 90 | 95 | 100 | 100 | 100 | 100 | 95 |
| ½ | 100 | 80 | 70 | 100 | 100 | 70 | 90 | 80 |
| ¼ | 95 | 50 | 20 | 80 | 100 | 50 | 70 | 20 |

DIGSA (*Digotaris sanguinalis*), SORBI (*Sorghum bicolor*), ECGCG (*Echinochloa crus-galli*), SOLNI (*Solanum nigrum*), AESIN (*Aeschynomeme indica*), ABUTH (*Abutilon avicennae*), XANSI (*Xanthium strumarium*), CAGEH (*Calystegia japonica*)

Example 4

Measurement of Activity of Solvent Fraction from *Streptomyces* Scopuliridis Kr-001 Culture Broth after Foliage Treatment To measure a weed-killing ability of culture broth obtained in <Example 3> for each solvent fraction, an experiment was performed as follows.

Specifically, culture broth of a *Streptomyces scopuliridis* KR-001 strain was fractionated into hexane, ethyl acetate, butanol, and water layers. For foliage treatment to *Digotaris sanguinalis*, fractions for each solvent in concentrations of 8 µg mL$^{-1}$, 16 µg mL$^{-1}$, 32 µg mL$^{-1}$, 63 µg$^{-1}$, 125 µg mL$^{-1}$, 250 µg mL$^{-1}$ and 500 µg mL$^{-1}$ were used. After five days, the weed-killing ability was evaluated such that an external symptom and efficacy were evaluated through naked-eye inspection based on the phytotoxicity index.

Consequently, as shown in FIG. 3 and Table 4, the activity was not exhibited in hexane and water layers, while the activity was exhibited in the ethyl acetate and butanol layers. In particular, the strongest weed-killing ability was demonstrated in the ethyl acetate layer. The weed-killing ability on *Digotaris sanguinalis* in ethyl acetate concentrations of 8 µg mL$^{-1}$, 16 µg mL$^{-1}$, 32 µg mL$^{-1}$, 63 µg mL$^{-1}$, 125 µg mL$^{-1}$, 250 µg mL$^{-1}$ and 500 µg mL$^{-1}$ were respectively 80%, 90%, 95%, 100%, 100%, 100% and 100%. Thus, it has been proven that strong weed-killing abilities were exhibited. Yields of an active material for each solvent fraction were evaluated as 0.03% for the hexane fraction, 3.61% for the ethyl acetate fraction, 17.84% for the butanol fraction, and 73.67% for the water fraction (Table 4 and FIG. 3).

TABLE 4

Activity of *Streptomyces scopuliridis* KR-001 strain on *Digotaris sanguinalis* for each solvent fraction after foliage treatment under greenhouse condition

| Solvent layer | Weed-killing ability (%) | | | | | | |
|---|---|---|---|---|---|---|---|
| | 500 (µg mL$^{-1}$) | 250 | 125 | 63 | 32 | 16 | 8 |
| hexane | 0 | 0 | 0 | 0 | 0 | 0 | 0 |
| Ethyl acetate | 100 | 100 | 100 | 100 | 95 | 90 | 80 |
| Butanol | 80 | 70 | 50 | 20 | 0 | 0 | 0 |
| Water | 0 | 0 | 0 | 0 | 0 | 0 | 0 |

Example 5

Measurement of Effect of Fraction of Culture Broth of *Streptomyces Scopuliridis* KR-001 Strain after Soil Treatment To measure an effect of the fraction of culture broth of the strain of the present invention obtained in <Example 4> for soil treatment, an experiment was performed as follows.

Specifically, a day before treatment, four types of grass weeds (*Digotaris sanguinalis, Sorghum bicolor, Echinochloa crus-galli,* and *Agropyron amithii*) and five types of broad leaf weeds (*Solanum nigrum, Aeschynomeme indica, Abutilon avicennae, Xanthium strumarium,* and *Calystegia japonica*) were seeded and managed under the greenhouse condition (30/20±5, Light/Dark=14/10 hours). An ethyl acetate fraction of culture broth of a *Streptomyces scopuliridis* KR-001 strain was prepared to have concentrations of 2000 µg mL$^{-1}$, 1000 µg mL$^{-1}$, 500 µg mL$^{-1}$, 250 µg mL$^{-1}$, and 125 µg mL$^{-1}$, and spray-treated. After 15 days of treatment, external symptoms and efficacy were evaluated through naked-eye inspection based on the phytotoxicity index (0 to 100%).

Consequently, as shown in FIG. 4 and Table 5, a weed-killing ability, on subject weed species, of the ethyl acetate fraction in the concentration of 2000 μg mL$^{-1}$ was 95 to 100%, and also, a complete weed control activity (100%) was exhibited on whole weed species except for *Sorghum bicolor* and *Abutilon avicennae* in the concentration of 1000 μg mL$^{-1}$. In concentrations of 2000 μg mL$^{-1}$ and 1000 μg mL$^{-1}$, *Sorghum bicolor* and *Abutilon avicennae* appeared on (above ?) the ground, but they were burndown, while other weed species do not appear to the ground. It was assumed that these symptoms were exhibited because each weed seed was brought into contact to the ethyl acetate fraction passing through the treatment layer after germination thereby being burndown. Among test subject weed species, it has been proven that *Digotaris sanguinalis, Agropyron amithii, Solanum nigrum, Xanthium strumarium,* and *Calystegia japonica* were completely burndown at the concentration of 500 μg mL$^{-1}$, and also that *Agropyron amithii* and *Calystegia japonica* were completed burndown at the concentrations of 250 μg mL$^{-1}$ (for *Agropyron amithii*) and 125 μg mL$^{-1}$ (for *Calystegia japonica*) which means that *Agropyron amithii* and *Calystegia japonica* were most susceptible species (FIG. 4 and Table 5).

Specifically, four types of grass weeds (*Digotaris sanguinalis, Sorghum bicolor, Echinochloa crus-galli,* and *Agropyron amithii*) and five types of broad leaf weeds (*solanum nigrum, Aeschynomeme indica, Abutilon avicennae, Xanthium strumarium,* and *Calystegia japonica*) were seeded and grown under a greenhouse condition for 9 days. Then, the ethyl acetate fraction of culture broth of the strain of the present invention obtained in <Example 4> was diluted and prepared to drug compounding liquid (including 50% acetone, and 0.1% Tween-20) such that the liquid has concentrations of 2000 μg mL$^{-1}$, 1000 μg mL$^{-1}$, 500 μg mL$^{-1}$, 250 μg mL$^{-1}$, 125 μg mL$^{-1}$, and 62.5 μg mL$^{-1}$ for spraying foliage treatment. After 12 days of treatment, external symptoms and efficacy were evaluated through naked-eye inspection based on the phytotoxicity index (0 to 100%).

Consequently, as shown in FIG. 5 and Table 5, weed-killing abilities on nine types of weeds at treatment concentration of 2000 μg mL$^{-1}$ and 1000 μg mL$^{-1}$, were 90 to 100%, indicating strong activity, and those at concentration of 500 μg$^{-1}$ were 80 to 100% which were good. An external symptom was exhibited at an initial phase of drug treatment, and an increased effect was exhibited with the lapse of time from treatment. The weed-killing ability was retained after 10 days of drug treatment. Thus, it has been proven that there was residual effect persistency. As a major symptom, a water

TABLE 5

Effect of ethyl acetate fraction of culture broth of *Streptomyces scopuliridis* KR-001 strain on four types of grass weeds (*Digotaris sanguinalis, Sorghum bicolor, Echinochloa crus-galli,* and *Agropyron amithii*) and five types of broad leaf weeds (*olanum nigrum, Aeschynomeme indica, Abutilon avicennae, Xanthium strumarium,* and *Calystegia japonica*) after soil treatment under greenhouse condition

| Concentration (μg mL$^{-1}$) | Weed-killing ability (%) | | | | | | | | |
|---|---|---|---|---|---|---|---|---|---|
| | DIGSA | SORBI | ECGCG | *Agropyron amithii* | SOLNI | AESIN | ABUTH | XANSI | CAGEH |
| 2000 | 100 | 95 | 100 | 100 | 100 | 100 | 95 | 100 | 100 |
| 1000 | 100 | 95 | 100 | 100 | 100 | 100 | 90 | 100 | 100 |
| 500 | 100 | 20 | 70 | 100 | 100 | 40 | 40 | 100 | 100 |
| 250 | 90 | 0 | 0 | 100 | 70 | 0 | 30 | 80 | 100 |
| 125 | 50 | 0 | 0 | 50 | 60 | 0 | 0 | 0 | 100 |
| 62.5 | 0 | 0 | 0 | 0 | 0 | 0 | 0 | 0 | 0 |

Example 6

Measurement of Activity of Fraction of Culture Broth of *Streptomyces scopuliridis* KR-001 Strain after Foliage Treatment To measure an effect of the fraction of culture broth of the strain of the present invention obtained in <Example 4> for foliage treatment, an experiment was performed as follows.

soaked spot was formed at an initial phase of treatment, and weeds were burnt down with time, and finally became dead leaves. It has been proven that depending on a weed species, a strong weed-killing ability was shown at the concentration of 250 μg mL$^{-1}$ or less, and that 95% or more of weed-killing abilities on *Sorghum bicolor, Solanum nigrum,* and *Aeschynomeme indica* were shown at the concentration of 62.5 μg mL$^{-1}$ (FIG. 5 and Table 6).

TABLE 6

Activity of ethyl acetate fraction on four types of grass weeds (*Digotaris sanguinalis, Sorghum bicolor, Echinochloa crus-galli,* and *Agropyron amithii*) and five types of broad leaf weeds (*Solanum nigrum, Aeschynomeme indica, Abutilon avicennae, Xanthium strumarium,* and *Calystegia japonica*) after foliage treatment under greenhouse condition

| Concentration (μg mL$^{-1}$) | Weed-killing ability (%) | | | | | | | | |
|---|---|---|---|---|---|---|---|---|---|
| | DIGSA | SORBI | ECGCG | *Agropyron amithii* | SOLNI | AESIN | ABUTH | XANSI | CAGEH |
| 2000 | 95 | 100 | 100 | 100 | 100 | 100 | 100 | 100 | 100 |
| 1000 | 95 | 100 | 95 | 100 | 100 | 100 | 100 | 100 | 100 |

TABLE 6-continued

Activity of ethyl acetate fraction on four types of grass weeds (*Digotaris sanguinalis*, *Sorghum bicolor*, *Echinochloa crus-galli*, and *Agropyron amithii*) and five types of broad leaf weeds (*Solanum nigrum*, *Aeschynomeme indica*, *Abutilon avicennae*, *Xanthium strumarium*, and *Calystegia japonica*) after foliage treatment under greenhouse condition

| Concentration ($\mu g\ mL^{-1}$) | Weed-killing ability (%) | | | | | | | | |
|---|---|---|---|---|---|---|---|---|---|
| | DIGSA | SORBI | ECGCG | Agropyron amithii | SOLNI | AESIN | ABUTH | XANSI | CAGEH |
| 500 | 90 | 80 | 100 | 100 | 100 | 100 | 95 | 100 | 100 |
| 250 | 80 | 100 | 60 | 90 | 100 | 100 | 70 | 100 | 100 |
| 125 | 50 | 100 | 40 | 90 | 100 | 100 | 40 | 90 | 100 |
| 62.5 | 40 | 95 | 20 | 80 | 95 | 100 | 30 | 90 | 70 |

Example 7

Evaluation of *Sicyos angulatus* Control Effect of Fraction of Culture Broth of *Streptomyces scopuliridis* KR-001 Strain after Foliage Treatment Under Greenhouse Condition To measure a control effect, on *Sicyos angulatus*, of the fraction of culture broth of the strain of the present invention obtained in <Example 4> after foliage treatment under a greenhouse condition, an experiment was performed as follows.

Specifically, *Sicyos angulatus*, which was grown to 3-leaf phase, was treated with the ethyl acetate fractions in concentrations of 2000 $\mu g\ mL^{-1}$ and 1000 $\mu g\ mL^{-1}$ through foliage treatment under the greenhouse condition. After 7 days, naked-eye inspection was performed.

Consequently, as shown in FIG. 6, it has been proven that as 24 hours passed after foliage treatment, an external symptom was started to exhibit, and *Sicyos angulatus* was completely suppressed at both concentrations (2000 μg and 1000 $\mu g\ mL^{-1}$) after five days (FIG. 6).

Example 8

Evaluation of *Sicyos Angulatus* Control Effect of Fraction of Culture Broth of *Streptomyces* Scopuliridis KR-001 Strain Through Transition into Body Under Greenhouse Condition To measure a *Sicyos angulatus* control effect of the fraction of culture broth of the strain of the present invention obtained in <Example 4> through transition to the body under a greenhouse condition, an experiment was performed as follows.

Specifically, *Sicyos angulatus* was seeded under the greenhouse condition. When $3^{rd}$ leaf was unfolded, a stem of the $3^{rd}$ leaf was topically treated by preparing gauze into which an ethyl acetate fraction prepared to have the concentration of 1000 $\mu g\ ml^{-1}$ is soaked, and then, being sealed together with the gauze using an aluminum foil. Then *Sicyos angulatus* was left under the dark condition for 24 hours for sufficiently absorption into a plant body. After hours of treatment, the gauze and aluminum foil were removed. Whether transition occurs or not was observed daily while *Sicyos angulatus* was managed under the same greenhouse condition. Naked-eye inspection was performed after six days of treatment.

Consequently, as shown in FIG. 7, it has been proven that an external symptom was stared to exhibit two days after topical treatment; and that after six days of treatment, untreated *Sicyos angulatus* was developed to 7-leaf phase, while treated *Sicyos angulatus* was developed to 4-leaf phase with burndown progressed from around of a second leaf, which is a lower leaf, and a forth leaf, which is an upper leaf. Therefore, it has been proven that upward transition and downward transition of the ethyl acetate fraction was simultaneously performed (FIG. 7).

Example 9

Evaluation of *Sicyos Angulatus* Control Effect of Fraction of Culture Broth of *Streptomyces Scopuliridis* KR-001 Strain after Foliage Treatment Under Field Condition To measure a *Sicyos angulatus* control effect of the fraction of culture broth of the strain of the present invention obtained in <Example 4> after foliage treatment, an experiment was performed as follows.

Specifically, as it has been proven that the ethyl acetate fraction of culture broth of the strain of the present invention obtained in <Example 4> showed a strong control effect, under the greenhouse condition, on *Sicyos angulatus*, which is an environmentally harmful plant designated as "Invasive Alien Plant" by Ministry of Environment, a field application test was performed under a practical field condition. A location for field test was the Namhangangbyeon region in front of a community hall located in 31-15 Angdeok-ri, Gaegun-myeon, Yangpyeong-gun, Gyeonggi-do, and the test period was from Sep. 22, 2011 to Oct. 6, 2011. As a growth situation when drug treatment was performed, *Sicyos angulatus* was in a 10-leaf phase to 15-leaf phase having the length of 2 m to 3 m. The treatment zone was 1 m×1 m, and 300 ml per each concentration was treated. The ethyl acetate fraction was weighted out such that final concentrations became 2000 $\mu g\ mL^{-1}$ and 4000 $\mu g\ mL^{-1}$. Then, the fraction was dissolved in a small amount of acetone, and diluted and prepared to drug compounding liquid (including 50% acetone, and 0.1% Tween-20). Then, naked-eye inspection was performed on 5, 8, and 14 days after treatment.

Consequently, as shown in FIG. 8 and Table 7, it has been exhibited that a weed-killing ability, on *Sicyos angulatus*, of the ethyl acetate fraction of culture broth of the strain of the present invention under the field condition was increased with the lapse of time after drug treatment, and that efficacy persistency was excellent such that *Sicyos angulatus* control effects, respectively, were 50%, 90%, and 100% (at the concentration of 4000 $\mu g\ mL^{-1}$) and 40%, 70% and 80% (at the concentration of 2000 $\mu g\ mL^{-1}$) on 5, 8, and 14 days after treatment. Typically, it has been known that a material having a weed-killing activity derived from a natural substance is fast-acting, so that efficacy is started to exhibit few hours after drug treatment, and efficacy duration is short and thus regeneration occurs certain times after drug treatment. However, it has been proven that the ethyl acetate fraction retains a weed-killing ability after two weeks which indicates a property of having excellent persistency in efficacy. Further, in consideration of a symptom in which a stem positioned at a lower part of a leaf treated with the drug is broken as damping-off, in addition to the leaf treated with the drug, it has been determined that there is transition into the lower stem (FIG. 8 and Table 7).

TABLE 7

Effect of ethyl acetate fraction of culture broth of *Streptomyces scopuliridis* KR-001 strain on *Sicyos angulatus* after foliage treatment under field condition

| Concentration | Weed-killing ability (%) | | |
|---|---|---|---|
| ($\mu$g mL$^{-1}$) | 5 DAT | 8 DAT | 14 DAT |
| 4000 | 50 | 90 | 100 |
| 2000 | 40 | 70 | 80 |

DAT: Days after treatment

Example 10

Weed Control Effect of Fraction of Culture Broth of *Streptomyces Scopuliridis* KR-001 Strain on Hard-to-Control Weeds (*Humulus japonicus, Artemisia princes, Equisetum arvense* and *Trifolium repens*) after Foliage Treatment To evaluate a weed-control effect, on hard-to control weeds such as *Humulus japonicus, Artemisia princes, Equisetum arvense* or *Trifolium repens*, of the fraction of culture broth of the strain of the present invention obtained in <Example 4> under a field condition, an experiment was performed as follows.

Specifically, test was performed on a selected region where weeds to be tested were naturally grown around filed of Korea Research Institute of Chemical Technology in Yuseong-gu, Daejeon, and test period was from Oct. 4, 2011 to Oct. 16, 2011. The treatment zone was 1 m×1 m, and 200 mL per each concentration was treated. The ethyl acetate fraction of culture broth of the strain of the present invention obtained in <Example 4> was weight out such that final treatment concentrations became 2000 $\mu$g mL$^{-1}$ and 4000 $\mu$g mL$^{-1}$. Then, the resultant was dissolved in a small amount of acetone, diluted and prepared to drug compounding liquid (including 50% acetone, 0.1% Tween-20), and treated. Naked eye inspection was performed on 5, 10 and 15 days after drug treatment (for *Humulus japonicus*), 5, 8 and 10 days after (for *Artemisia princes* and *Equisetum arvense*) and 4, 8, 12 days after (for *Trifolium repens*).

<10-1> Evaluation of *Humulus japonicas* Control Effect

As shown in FIG. 9 and Table 8, the ethyl acetate fraction of culture broth of the strain of the present invention obtained in <Example 4> showed an excellent weed control effect on *Humulus japonicus*, in which after five days of treatment in the concentrations of 2000 $\mu$g mL$^{-1}$ and 4000 $\mu$g mL$^{-1}$, a weed control effect of about 40% and 30% were respectively exhibited, and then the effect was rapidly enhanced, so that after 10 days, 100% and 95% were respectively exhibited, and after 15 days 100% of the weed-killing ability was exhibited in both treatment concentrations (Table 8 and FIG. 9). The weed-killing ability was continuously increased with the lapse of time same as the symptom shown in *Sicyos angulates*, so that the weed-killing ability is retained for 15 days after treatment. Thus, it has been proven that there is a property of retaining an efficacy persistent effect.

TABLE 8

Effect of ethyl acetate fraction on *Humulus japonicus, Artemisia princeps, Equisetum arvense* and *Trifolium repens* after foliage treatment under field condition

| | Weed-killing ability (%) | | | |
|---|---|---|---|---|
| Concentration ($\mu$g mL$^{-1}$) | Humulus japonicus | Artemisia princes | Equisetum arvense | Trifolium repens |
| 4000 | 100 | 100 | 100 | 100 |
| 2000 | 100 | 100 | 100 | |

<10-2> Evaluation of *Artemisia princeps* Control Effect

As shown in FIG. 10 and Table 8, the ethyl acetate fraction of culture broth of the strain of the present invention obtained in <Example 4> showed an excellent *Artemisia princeps* control effect, such that a complete *Artemisia princes* control effect was exhibited in concentrations of 2000 $\mu$g mL$^{-1}$ and 4000 $\mu$g mL$^{-1}$. The effect was started to exhibit on three days after treatment. After five days, in the concentration of 4000 $\mu$g mL$^{-1}$ complete control effect was exhibited, while 80% was controlled in the concentration of 2000 $\mu$g mL$^{-1}$. Then, after 8 days, the weed-control in both concentrations was 100% so that it has been proven that the weed-killing ability was retained (Table 8 and FIG. 10).

<10-3> Evaluation of *Equisetum arvense* Control Effect

As shown in FIG. 11 and Table 8, the ethyl acetate fraction of culture broth of the strain of the present invention obtained in <Example 4> showed an excellent *Equisetum arvense* control effect, such that 95% and 90% of weed-killing abilities were respectively exhibited in concentrations of 4000 $\mu$g mL$^{-1}$ and 2000 $\mu$g mL$^{-1}$ on five days after treatment due to rapid expression of efficacy, and complete burndown was exhibited after 8 days (Table 8 and FIG. 11).

<10-4> Evaluation of *Trifolium repens* Control Effect

As shown in FIG. 12 and Table 8, the ethyl acetate fraction of culture broth of the strain of the present invention obtained in <Example 4> showed an excellent *Trifolium repens* control effect such that spots were formed and advanced on 4 days after treatment, and leaves were completely burndown after 8 days. Then, even a stem was burndown after 12 days. Therefore, it has been proven that a weed-killing ability was retained and the speed of efficacy expression is rapid as well (Table 8 and FIG. 12).

Example 11

Evaluation of Crop-Selectivity of Fraction of Culture Broth of *Streptomyces Scopuliridis* KR-001 Strain Under Greenhouse Condition To evaluate crop-selectivity of the fraction of culture broth of the strain of the present invention obtained in <Example 4>, an experiment was performed as follows.

Specifically, crop-selectivity of the ethyl acetate fraction of culture broth of the strain of the present invention obtained in <Example 4> was evaluated, wherein excellent weed-killing abilities of the fraction on various types of weeds including *Sicyos angulates* were evaluated. Subject crops were three types of grass crops such as rice, wheat, and barley and two types of broad leaf crops such as hot peppers and tomatoes. A growth situation of each crop at time of treatment was as follows: 3.5 leaves for rice; 1.2 leaves for wheat; 1 leaf for barley; 3.7 leaves for hot peppers; and 4.4 leaves for tomatoes. Treatment concentrations were 4000 µg mL$^{-1}$, 2000 µg mL$^{-1}$, 1000 µg mL$^{-1}$, 500 µg mL$^{-1}$, 250 µg mL$^{-1}$ and 125 µg mL$^{-1}$. A phytotoxicity degree for crops was evaluated through naked-eye inspection after 14 days of treatment.

Consequently, as shown in FIG. 13 and Table 9, phytotoxicity was induced in all five types of subject crops so that it has been proven that there was no crop-selectivity. In particular, severe phytotoxicity was induced in hot peppers and tomatoes, which are broad leaf corps, such that 100% of phytotoxicity, which is the most severe, was induced in tomatoes in a whole range of treated concentration, and 70 to 100% of phytotoxicity was induced in hot peppers in a range of treatment. Relatively low phytotoxicity was induced in broad leaf corps such that 50 to 80% was exhibited for barley in the range of treated concentration, and 30% or less of phytotoxicity, which was relatively low, was induced in rice and wheat. Therefore, it has been proven that a material having a weed-killing activity derived from *actinomyces* has no crop-selectivity, and thus the material should be non-selectively used (FIG. 13 and Table 9).

TABLE 9

Phytotoxicity, on three types of grass corps such as rice, wheat, and barley and two types of broad leaf corps such as hot peppers and tomatoes, of ethyl acetate fraction of culture broth of *Streptomyces scopuliridis* KR-001 strain on greenhouse condition

| Crop | Phytotoxicity (%) | | | | | |
|---|---|---|---|---|---|---|
| | 4000 (µg mL$^{-1}$) | 2000 | 1000 | 500 | 250 | 125 |
| Rice | 30 | 30 | 10 | 10 | 5 | 0 |
| Wheat | 30 | 30 | 30 | 20 | 20 | 20 |
| Barley | 80 | 80 | 80 | 70 | 60 | 50 |
| Hot peppers | 90 | 90 | 90 | 90 | 80 | 70 |
| Tomatoes | 100 | 100 | 100 | 100 | 100 | 100 |

Example 12

Comparison of Weed-Killing Abilities of Fraction of Culture Broth of *Streptomyces Scopuliridis* KR-001 Strain and Control Compound To evaluate weed-killing ability of the fraction of culture broth obtained in <Example 4>, weed-killing abilities of bialaphos and glufosinate were compared together.

Specifically, bed soil for gardening was placed into a plastic square pot having a surface area of 350 cm$^2$, and four types of grass weeds including *Digotaris sanguinalis*, and three types of broad weeds including *Solanum nigrum* were respectively seeded under the greenhouse condition (25±3, 14/10 h=Light/dark). After 15 days of seeding, the ethyl acetate fraction of culture broth, bialaphos, and glufosinate were diluted and prepared to drug compounding liquid (containing 50% acetone, and 0.1% Tween-20) such that concentrations became 250, 500 and 1000 µg mL$^{-1}$. Then, the drug compounding liquid was treated to foliage in an amount of 14 ml/pot. Thereafter, the weed-killing ability was evaluated through naked-eye inspection.

Consequently, as shown in FIG. 14, it has been proven that the ethyl acetate fraction of culture broth of the strain of the present invention obtained in <Example 4>, bialaphos, and glufosinate showed the similar level of weed-killing abilities in concentrations of 250 µg mL$^{-1}$, 500 µg mL$^{-1}$ and 1000 µg mL$^{-1}$ (FIG. 14). Thus, it has been determined that the weed-killing ability of the ethyl acetate fraction of culture broth of the strain of the present invention was similar to that of bialaphos or glufosinate which were control compounds.

Example 13

Evaluation of Material Having Weed-Killing Activity in Fraction of Culture Broth of *Streptomyces Scopuliridis* KR-001 Strain To evaluate a material having a weed-killing activity in fraction of culture broth of the strain of the present invention obtained in <Example 4>, an experiment was performed as follow.

Specifically, HPLC was performed on the ethyl acetate fraction of culture broth of the strain of the present invention obtained in <Example 4>. The analysis condition was as follows (Table 10).

As a result, peaks were identified at 6 min 50 sec, 9 min 10 sec, and 15 min 30 sec under Rt. (FIG. 15).

TABLE 10

HPLC analysis condition of ethyl acetate fraction of culture broth of *Streptomyces scopuliridis* KR-001 strain

| Solvent | 40% MeOH |
|---|---|
| Column | C-18 |
| Temperature | 40 |
| Flow | 1 ml/min |
| UV | 254 nm |

Example 14

Evaluation of Compound of Ethyl Acetate Active Material Fraction of Culture Broth of *Streptomyces scopuliridis* KR-001 Strain and Weed-Killing Ability Thereof To evaluate compounds obtained at 6 min 50 sec, 9 min 10 sec, and 15 min 30 sec under Rt., in <Example 12>, and weed-killing abilities thereof, an experiment was performed as follows.

Specifically, prep-HPCL was performed on compounds obtained at 6 min 50 sec, 9 min 10 sec, and 15 min 30 sec under Rt., in <Example 12> with the analysis condition as above (Table 10), and compounds were divided to fr. 1 to 7. *Digotaris sanguinalis* was treated with each fraction in concentrations of 112.5 µg mL$^{-1}$, 225 µg mL$^{-1}$, 450 µg mL$^{-1}$ and 900 µg mL$^{-1}$ by foliage treatment. The weed-killing ability was evaluated after five days such that an external symptom and efficacy were evaluated through naked-eye inspection based on the phytotoxicity index.

Consequently, as shown in FIGS. 16 and 17, an excellent weed-killing ability was shown in fr. 3, 4, and 5. Fr. 3, 4, and 5, which showed the excellent weed-killing ability, were isolated and purified. Thereafter, structures at 6 min 50 sec, 9 min 10 sec, and 15 min 30 sec under Rt., were established as herbicidin B, herbicidin A and herbicidin F through data comparison with documents (see *The Journal of Antibiotics* 1982, 35 1711-1714.) (FIGS. 16 and 17).

Example 15

Investigation of Optimal Carbon Source for Medium for Industrial Mass Production of *Streptomyces Scopuliridis* KR-001 Strain To reduce production cost by simplifying a compositional component of the bennet medium described in [Table 2], which was a culture medium of a *Streptomyces scopuliridis* KR-001 strain, and to efficiently and massively culture the *Streptomyces scopuliridis* KR-001 strain, an experiment was performed for selecting a suitable medium for microorganism growth and production of a material having a weed-killing activity among various carbon sources industrially used during microorganism culture.

Specifically, 0.5% (w/v) of soy peptone (5 g/L) was added to a 500 ml and baffled flask to prepare a minimal nutrition medium. Then, glucose, sucrose, soluble starch, potato starch, corn starch, maltose and molasses (1.0% (w/v) (10 g/L) for each), which were industrial raw materials, were respectively added. Thereafter, the resultant was inoculated with 2% of precultured culture broth in <Example 1>, and shake-cultured for five days at 27 with 170 rpm. Final pH and a degree of microorganism growth for each culture broth were measured. To evaluate a weed-killing activity, the culture filtrate, in which bacteria were completely removed, was diluted to 8 times (including 0.1% Tween-20). The diluents were sprayed to *Digotaris sanguinali* for foliage treatment under the greenhouse condition (30±5, light/dark=14 hours/10 hours). After three days, naked-eye inspection was performed based on an external symptom and a degree of the weed-killing ability (0; no effect, 100; complete control). In addition, as a control, 500 ml of bennet liquid medium described in [Table 2] was added to a 500 d baffled flask. Then, the medium was inoculated with 2% of precultured culture broth in <Example 1>, and shake-cultured for five days at 27 with 170 rpm.

Consequently, as shown in Table 11 and FIG. 18, it has been found that: comparing with bennet medium culture broth, a medium, to which potato starch, corn starch, and maltose were added, showed very excellent bacterial growth and the weed-killing activity about 70%; and that a medium, to which soluble starch was added, showed bacterial growth similar to that of the bennet medium, and an excellent weed-killing activity which was 60%. In addition, it has been proven that the medium, to which potato starch, corn starch and maltose were added, which showed relatively high weed-killing activities, has pH fallen within a range of 6 to 7, and very good (+++) bacterial growth. On the other hand, pH of the medium, to which carbon sources such as sucrose and molasses were added, having a relatively low weed-killing activity, i.e., 20%, had high pH which is around 9, and showed bacterial growth in a normal level (++). Thus, through the result, it has been proven that: a produced amount of a material having the weed-killing activity or types of metabolites were varied depending on a type of carbon sources; pH of culture filtrate was affected by the variance; and, ultimately, the produced amount of the active material was highest around pH 5 to 7 thereby exhibiting the relatively high weed-killing activity (Table 11 and FIG. 18).

TABLE 11

Weed-killing activity of culture filtrate of *Streptomyces scopuliridis* KR-001 strain depending on type of carbon sources

| Basal medium | 1% (w/v) carbon source (10 g/L) | Final pH | Weed-killing activity[a] | Bacteria growth[b] |
|---|---|---|---|---|
| 0.5% (w/v) Soy peptone (5 g/L) | Glucose | 8.06 | 50 | +++ |
| | Sucrose | 9.22 | 20 | ++ |
| | Soluble starch | 7.57 | 60 | ++ |
| | Patato starch | 7.01 | 70 | +++ |
| | Corn starch | 5.86 | 70 | +++ |
| | Maltose | 6.1 | 70 | +++ |
| | Molasses | 8.91 | 20 | ++ |
| Bennet medium | | 9.17 | 20 | ++ |

[a] 0; no effect, 100; complete control.
[b] +++; very good, ++; normal, +; poor.

Example 16

Investigation of Optimal Nitrogen Source of Medium for Industrial Mass Production of *Streptomyces Scopuliridis* KR-001 Strain As described in <Example 15>, to reduce production cost by simplifying a compositional component of the bennet medium, which was a culture medium of a *Streptomyces scopuliridis* KR-001 strain, and to efficiently and massively culture the *Streptomyces scopuliridis* KR-001 strain, an experiment was performed for selecting a suitable medium for microorganism growth and production of a material having a weed-killing activity among various nitrogen sources industrially used during microorganism culture.

Specifically, a basal medium, to which 2% glycerol (20 ml/L) was added as a carbon source, was prepared in a 500 ml baffled flask, and then 0.5% (w/v) (5 g/L) of organic form nitrogen sources such as skim milk, tryptone, a beef extract, peptone, corn steep liquor (CSL), soybean powder, casein peptone, a yeast extract, and soy peptone were added. Thereafter, the medium was inoculated with 2% of precultured culture broth in <Example 1>, and then shake-cultured for five days at 27 with 170 rpm. The culture broth was investigated for microorganism growth and the weed-killing activity by the method same as <Example 15>. In addition, as a control, 500 ml and of bennet medium described in [Table 2] was placed to a 500 ml and baffled flask, and inoculated with 2% of precultured culture broth in <Example 1>. Then, the resultant was shake-cultured for five days at 27 with 170 rpm.

Consequently, as shown in Table 12 and FIG. 19, when a yeast extract and a beef extract were added as nitrogen sources, bacerial growth was very good (+++); 40 to 50% of weed-killing ability was exhibited when 8-fold diluents of culture filtrate was treated; and final pH fell within a range of 6 to 7 same as that of a carbon source. Thus, it has been proven that there is close correlation between bacterial growth and pH of culture filtrate for each nitrogen source. Meanwhile, in the case where soybean powder was added, bacterial growth was normal (++), however, the weed-killing activity was the similar level to that of yeast extract or beef extract added medium. Generally, bacterial growth and an amount of a produced secondary metabolite are mostly proportional. However, depending on culture circumstance, a case often occurs where only the number of cells increases and production of a secondary metabolite is substantially small, and in the contrary, there is a case where bacterial growth is relatively poor, however an amount of a produced secondary metabolite was relatively much large. Since the medium including soybean powder added thereto showed normal bacterial growth but an excellent weed-killing activity, it has been proven that production of an active material exhibiting the weed-killing ability was vigorously performed (Table 12 and FIG. 19).

TABLE 12

Weed-killing activity of culture filtrate of *Streptomyces scopuliridis* KR-001 strain depending on type of nitrogen sources

| Basal medium | 0.5% (w/v) Nitrogen source (5 g/L) | Final pH | Weed-killing activity[a] | Bacteria growth[b] |
|---|---|---|---|---|
| 2% (w/v) Glycerol (20 ml/L) | Skim milk | 8.01 | 10 | + |
| | Tryptone | 7.95 | 10 | ++ |
| | Beef extract | 7.17 | 40 | +++ |
| | Peptone | 8.29 | 10 | + |
| | Corn steep liquor | 6.95 | 30 | ++ |
| | Soybean powder | 5.92 | 40 | ++ |
| | Casein peptone | 8.35 | 10 | + |
| | Yeast extract | 5.9 | 50 | +++ |
| | Soy peptone | 8.17 | 10 | ++ |
| Bennet medium | | 9.17 | 20 | ++ |

[a]0; no effect, 100; complete control.
[b]+++; very good, ++; normal, +; poor.

Example 17

Selection of Optimal Medium for Industrial Mass Production of *Streptomyces Scopuliridis* KR-001 Strain By combining the carbon source and the nitrogen source having an excellent weed-killing activity selected in <Example 15> and <Example 16> among industrial medium components, an optimal medium was selected for production of a material of a *Streptomyces scopuliridis* KR-001 strain having the weed-killing activity.

Specifically, to a 500 and baffled flask, were added 1% (w/v) of potato starch and corn starch or maltose, which were carbon sources, and 0.5% (w/v) of a beef extract, soybean powder, or a yeast extract, which were nitrogen sources, wherein the carbon source and the nitrogen source were selected in <Example 15> and <Example 16> and had an excellent weed-killing activity. Then, the flask was inoculated with 2% of precultured culture broth in <Example 1>. An initial pH of each medium was adjusted to 6.95 to 7.10. Thereafter, the resultant was shake-cultured for five days at 27, with 170 rpm. To evaluate the weed-killing activity for each medium, as described in <Example 15>, *Digotaris sanguinalis* was treated by spraying foliage treatment. After three days, naked-eye inspection (0; no effect, 100; complete control) was performed based on an external symptom and a degree of the weed-killing ability. In addition, as a control, 500 ml of bennet medium described in [Table 2] was placed to a 500 ml baffled flask, and the flaks was inoculated with 2% of precultured culture broth in <Example 1>. Then, the resultant was shake-cultured for five days at 27 with 170 rpm.

Consequently, as shown in Table 13 and FIG. 20, it has been proven that: when corn starch was used as a carbon source, the weed-killing activity was relatively higher on day 5 of culture, however, the weed-killing activity tended to be lower on day 7 of culture; when potato starch was used, the weed-killing activity on day 5 of culture was slightly lower than that of corn starch, however, the activity was constantly maintained on 7 day of culture; and when maltose was used, the relatively low weed-killing activity was exhibited. Further, when soybean powder was used as a nitrogen source, regardless of a type of carbon sources, it has been proven that bacterial growth was mostly good, and the weed-killing activity was the relatively higher. When correlation between final pH of culture filtrate, bacterial growth, and the weed-killing activity was analyzed, it has been proven that bacterial growth was very good (+++) and the weed-killing activity was high in low pH same as results in <Example 15> and <Example 16>. Thus, from the result in <Example 15>, potato starch, as a carbon source, and soybean powder, as a nitrogen source, were finally selected for culture of the *Streptomyces scopuliridis* KR-001 strain in consideration of production of a material having the weed-killing activity, stability, and reduction in a period of culture (Table 13 and FIG. 20).

TABLE 13

Weed-killing activity of culture filtrate of *Streptomyces scopuliridis* KR-001 strain depending on combination of carbon sources and nitrogen sources

| 1% (w/v) carbon source (10 g/L) | 0.5% (w/v) Nitrogen Source (5 g/L) | pH 5-day culture | pH 7-day culture | Weed-killing activity[a] 5-day culture | Weed-killing activity[a] 7-day culture | Bacteria growth[b] |
|---|---|---|---|---|---|---|
| Patato starch | Beef extract | 8.75 | 8.86 | 50 | 50 | +++ |
| | Soybean powder | 5.68 | 6.96 | 90 | 90 | +++ |
| | Yeast extract | 8.41 | 8.86 | 50 | 40 | +++ |
| Corn starch | Beef extract | 8.31 | 8.7 | 90 | 50 | ++ |
| | Soybean powder | 5.62 | 5.62 | 90 | 80 | +++ |
| | Yeast extract | 8.26 | 8.43 | 70 | 60 | +++ |
| Maltose | Beef extract | 8.78 | 9.09 | 50 | 50 | + |
| | Soybean powder | 5.83 | 6.62 | 80 | 60 | ++ |
| | Yeast extract | 8.87 | 9.04 | 30 | 60 | ++ |
| Bennet medium | | 5.74 | 5.15 | 80 | 90 | ++ |

[a]0; no effect, 100; complete control.
[b]+++; very good, ++; normal, +; poor.

Example 18

Optimal Medium Composition for Industrial Mass Production of *Streptomyces scopuliridis* Kr-001 Strain By determining an optimal ratio of potato starch and soybean powder, and an weed-killing activity depending on the ratio, an optimal medium composition was established which was most suitable for production of a material having the weed-killing activity of a *Streptomyces scopuliridis* KR-001 strain, wherein the potato starch was a finally selected carbon source, and soybean powder was a finally selected nitrogen source selected in <Example 17>.

Specifically, by the method same as <Example 15> and <Example 17>, a medium was prepared by adding 1 to 3% (w/v) of potato starch and 0.5 to 2% (w/v) of soybean powder, wherein the potato starch was a finally selected carbon source and the soybean powder was a finally selected nitrogen source selected in <Example 15>, <Example 16> and <Example 17>. In addition, by the method as described above, potato starch and glucose (1% (w/v) (10 g/L) for each), as carbon sources, and soybean powder (1% (w/v) (10 g/L)), as a nitrogen source, were added. Then, 2% of precultured culture broth in <Example 1> was inoculated. Then, each medium was shake-cultured for five days at 27 with 170 rpm. To quantify content of the material having the weed-killing activity in each culture medium, materials A and B, which were produced by the *Streptomyces scopuliridis* KR-001 strain and had the weed-killing activity, were prepared for each concentration. Then, through HPLC analysis under the condition described in [Table 14] below, under areas of peak exhibited for each concentration were quantified to construct calibration curve. Thereafter, contents of A and B in each culture medium were quantified through HPLC analysis, wherein A and B were materials having the weed-killing activity. HPLC analysis of A and B, which were materials having the weed-killing activity, for each concentration was triplicated. HPLC analysis was performed by using Shimadzu ODS column (4.6×300 mm) and 35% methanol, as a mobile phase, at 245 nm to establish an optimal medium composition and culture condition.

TABLE 14

| \multicolumn{2}{c}{HPLC analysis condition} |
| --- | --- |
| | Condition |
| Column | Shimadzu ODS (4.6 × 300 mm) |
| Mobile phase | A:B = 35:65<br>Material A mobile phase: Methanol (Methyl alcohol)<br>Material B mobile phase: distilled water |
| Time | 30 min |
| Flow rate | 1 ml/min |
| Detection wavelength | UV 254 nm |
| Amount of injection | 20 μl |
| Temperature of column | 40 |

Consequently, as shown in Table 15 and FIG. 21, it has been proven that: an amount of produced A, a material having a the weed-killing activity, was 734.27 μg/m in combination of 3% of potato starch and 2% of soybean powder (C/N ratio=2:1) which was the highest and six times more than that of the bennet medium (131.13 μg/mL); and production unit cost for the combination was 174.60 won which was 13 times lower than that of the bennet medium (2,240.92 won). For B, a material having the weed-killing activity, it has been proven that: the highest value, i.e., 64.32 μg/mL was shown in combination of 2% of potato starch and 2% of soybean powder (C/N ratio=1:1); however, an amount of production tended to be increased as amount of soybean powder increased irrelevant to a concentration of potato starch. In addition, it has been proven that: although a medium having combination of potato starch and glucose (1% for each), as carbon sources, and soybean powder (1%) (C/N ratio 2=1) showed cheaper production cost than the medium having combination of 3% of potato starch and 2% of soybean powder (C/N ratio=2:1), an amount of produced A, which was a material having the weed-killing activity, was small (Table 15 and FIG. 21).

TABLE 15

Comparison of production of material having weed-killing activity of *Streptomyces scopuliridis* KR-001 strain depending on ratio of carbon source and nitrogen source

| Medium composition | | Unit coast of medium (won/L) | Consist of materials having weed-killing activity (μg/mL) | |
| --- | --- | --- | --- | --- |
| Carbon source | Nitrogen source | | Active material A | Active material B |
| 1% (w/v) Potato starch (10 g/L) | 0.5% (w/v) Soybean powder (5 g/L) | 54.45 | 133.48 | 4.91 |
| | 1.0% (w/v) Soybean powder (10 g/L) | 65.7 | 131.73 | 36.85 |
| | 2.0% (w/v) Soybean powder (20 g/L) | 88.2 | 44.08 | 62.21 |
| 2% (w/v) Potato starch (20 g/L) | 0.5% (w/v) Soybean powder (5 g/L) | 97.65 | 175.61 | 4.73 |
| | 1.0% (w/v) Soybean powder (10 g/L) | 108.9 | 434.15 | 8.09 |
| | 2.0% (w/v) Soybean powder (20 g/L) | 131.4 | 419.02 | 64.32 |
| 3% (w/v) Potato starch (30 g/L) | 0.5% (w/v) Soybean powder (5 g/L) | 140.85 | 182.2 | 6.13 |
| | 1.0% (w/v) Soybean powder (10 g/L) | 152.1 | 339.92 | 7.96 |
| | 2.0% (w/v) Soybean powder (20 g/L) | 174.6 | 734.27 | 23.96 |
| 1% (w/v) Potato starch (10 g/L) 1% (w/v) Glucose (10 g/L) | 1.0% (w/v) Soybean powder (10 g/L) | 83.2 | 566.27 | 14.98 |
| Bennett's medium | | 2,240.92 | 131.13 | 15.03 |

Thus, from the result in <Example 18>, an optimal medium was established which is most suitable for production of a material having the weed-killing activity of the *Streptomyces scopuliridis* KR-001 strain, and the optimal medium composition and culture condition were described in [Table 16] below.

TABLE 16

Optimal medium composition and culture condition of *Streptomyces scopuliridis* KR-001 strain

| Medium composition | | Culture condition | | |
| --- | --- | --- | --- | --- |
| Carbon source | Nitrogen source | pH | Temperature of culture | Period of culture |
| Potato starch 3% | Soybean powder 2% | Initial pH of 6.95 to 7.10 | 27 | 5 days |

Example 19

Evaluation of Effect of Weed-Killing Activity of Optimal Medium for Industrial Mass Production of *Streptomyces scopuliridis* KR-001 Strain To evaluate an effect of the optimal medium for mass culture of a *Streptomyces scopuliridis* KR-001 strain in <Example 18>, a weed-killing activity was investigated.

Specifically, culture broth, in which the *Streptomyces scopuliridis* KR-001 strain was cultured by using the Bennett's medium described in [Table 2], and culture broth, in which the *Streptomyces scopuliridis* KR-001 strain was cultured by using the optimal medium in <Example 18> were diluted to 8 times. Then, *Digitaris sanguinalis* was treated with the diluents by spraying foliage treatment under a greenhouse condition. After three days, an external symptom was evaluated.

Consequently, as shown in FIG. 22, it has been proven that culture broth, in which the *Streptomyces scopuliridis* KR-001 strain was cultured with the optimal medium, showed a significantly strong weed-killing ability with respect to untreated or culture broth cultured by using the Bennett's medium (FIG. 22).

[Accession Number]

Name of deposition organ: Korea Research Institute of Bioscience and Biotechnology (KRIBB)

Accession number: KCTC12156BP

Deposition date: 20120309

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for weed control comprising treating weeds or a seed or a habitat thereof with any one or more selected from the group consisting of the *Streptomyces scopuliridis* KR-001 strain deposited under accession number KCTC 12156BP, culture broth thereof, an extract of the culture broth, and an active fraction of the extract.

2. The method as set forth in claim 1, wherein the fraction is obtained by sequentially fractionating the extract of the culture broth by using hexane, ethyl acetate, butanol, and water as a solvent.

3. The method as set forth in claim 1, wherein the active fraction is a fraction obtained at 6 to 7 min, 8 to 10 min, or 15 to 17 min by eluting the fraction of the culture broth from column chromatography by using 40% aqueous methanol solution.

4. The method as set forth in claim 1, wherein the weeds are grass weeds, broadleaf weeds, or hard-to-control weeds.

5. The method as set forth in claim 4, wherein the grass weeds are any one selected from the group consisting of *Digitaris sanguinalis, Sorghum bicolor, Agropyron smithii* and *Echinochloa crus-galli*.

6. The method as set forth in claim 4, wherein the broadleaf weeds are any one selected from the group consisting of *Solanum nigrum, Aeschynomeme indica, Abutilon avicennae, Xanthium strumarium* and *Calystegia japonica*.

7. The method as set forth in claim 4, wherein the hard-to-control weeds are any one selected from the group consisting of *Sicyos angulates, Humulus japonicus, Artemisia princeps, Equisetum arvense* and *Trifolium repens*.

* * * * *